(12) United States Patent
Xie et al.

(10) Patent No.: US 11,312,717 B2
(45) Date of Patent: Apr. 26, 2022

(54) ORGANIC NANO-GRID, NANO-POLYMER THEREOF AND PREPARATION METHOD THEREFOR

(71) Applicant: NANJING UNIVERSITY OF POSTS AND TELECOMMUNICATIONS, Jiangsu (CN)

(72) Inventors: Linghai Xie, Jiangsu (CN); Wei Huang, Jiangsu (CN); Ying Wei, Jiangsu (CN); Dongqing Lin, Jiangsu (CN); Quanyou Feng, Jiangsu (CN); Hui Liu, Jiangsu (CN); Chunxiao Zhong, Jiangsu (CN)

(73) Assignee: NANJING UNIVERSITY OF POSTS AND TELECOMMUNICATIONS, Jiangsu (CN)

( * ) Notice: Subject to any disclaimer, the term of this patent is extended or adjusted under 35 U.S.C. 154(b) by 0 days.

(21) Appl. No.: 16/766,301

(22) PCT Filed: Jan. 26, 2018

(86) PCT No.: PCT/CN2018/074317
§ 371 (c)(1),
(2) Date: May 22, 2020

(87) PCT Pub. No.: WO2019/100582
PCT Pub. Date: May 31, 2019

(65) Prior Publication Data
US 2021/0163482 A1 Jun. 3, 2021

(30) Foreign Application Priority Data
Nov. 24, 2017 (CN) .......................... 201711188236.2

(51) Int. Cl.
*C07D 471/22* (2006.01)
*C08G 61/12* (2006.01)
*B82Y 30/00* (2011.01)

(52) U.S. Cl.
CPC ......... *C07D 471/22* (2013.01); *C08G 61/124* (2013.01); *B82Y 30/00* (2013.01);
(Continued)

(58) Field of Classification Search
CPC ............... C07D 471/22; C08G 61/124; C08G 2261/18; C08G 2261/3142; C08G 2261/3241; C08G 2261/45; B82Y 30/00
See application file for complete search history.

(56) References Cited

FOREIGN PATENT DOCUMENTS

| CN | 106496527 | 3/2017 |
|---|---|---|
| EP | 2180014 | 4/2010 |

(Continued)

OTHER PUBLICATIONS

"International Search Report (Form PCT/ISA/210) of PCT/CN2018/074317," dated Sep. 3, 2018, with English translation thereof, pp. 1-4.

*Primary Examiner* — Shane Fang
(74) *Attorney, Agent, or Firm* — JCIP Global Inc.

(57) ABSTRACT

The present invention provides an organic nano-grid, a nano-polymer thereof and a preparation method therefor. The organic nano-grid has a general formula (I), and the nano-polymer has a general formula (II), wherein $R_1$ is an alkyl chain, $R_2$ is halogen or an electroactive group, and X may comprise a heteroatom such as N, O and S, and n is a natural number from 1 to 10. A nano-connection strategy is applied to the construction of a one-dimensional nano-polymer. The polymer starts from a monomer $A_2B_2$ to form a corresponding nano-polymer by a Friedel-Crafts polymerization cyclization reaction.

3 Claims, 11 Drawing Sheets

(52) U.S. Cl.
CPC ... *C08G 2261/18* (2013.01); *C08G 2261/3142* (2013.01); *C08G 2261/3241* (2013.01); *C08G 2261/45* (2013.01)

(56) References Cited

FOREIGN PATENT DOCUMENTS

| | | |
|---|---|---|
| JP | 2004091444 | 3/2004 |
| KR | 20130067177 | 6/2013 |
| WO | 2004099340 | 11/2004 |

ORGANIC NANO-GRID, NANO-POLYMER THEREOF AND PREPARATION METHOD THEREFOR

CROSS-REFERENCE TO RELATED APPLICATION

This application is a 371 of international application of PCT application serial no. PCT/CN2018/074317, filed on Jan. 26, 2018, which claims the priority benefit of China application no. 201711188236.2, filed on Nov. 24, 2017. The entirety of each of the above mentioned patent applications is hereby incorporated by reference herein and made a part of this specification.

BACKGROUND

Technical Field

The present disclosure belongs to the field of organic polymer semiconductor materials preparation and relates to an organic nanogrids, nanopolymers thereof and preparation methods therefor.

Description of Related Art

The connection mode of nano-scale molecular blocks is the core of building complex topological polymers. Efficient nano-connection needs to meet the following standards: (1) The ring-forming structure is singular during the chemical bond connection process; (2) The random cross-linking process is inhibited as much as possible. Among them, non-covalent bonds and reversible covalent bonds are current two major nano-connection modes. The characteristics of such connections are: the bond energy is relatively small (10~300 KJ/mol) (J. Am. Chem. Soc. 2016, 138, 3255), and a dynamic reversible process can be formed in the process of bond-forming and bond-breaking. This can help generate a corrective effect when dislocated cross-linking occurs, thereby forming an orderly structured nano-block, such as covalent/super molecular organic framework (Science, 2017, 355, 1585). However, this type of dynamically reversible nano-connection is only suitable for situations where the bond energy is small (such as multiple hydrogen bonds, B—O bonds, etc.) (Science, 2005, 310, 1166; Science, 2007, 316, 210.) and a few obviously dynamically reversible organic reactions (the commonly seen one is the nucleophilic addition reaction of aldehydes) (J. Am. Chem. Soc. 2017, 139, 2421). In contrast, for most C—C bond coupling reactions, it is difficult to establish an effective dynamic balance because it takes a lot of energy (at least 350 KJ/mol) to break a C—C bond. In this case, once a dislocated connection occurs, it is difficult to correct and restore it, so it will eventually lead to the generation of random cross-linked polymers. In addition, this type of dynamic reversible reaction is controlled by the thermodynamic process, requiring a long reaction time (at least three days) and harsh reaction conditions. This is not conducive to the mass production of nanopolymers. Therefore, it is very difficult to explore efficient nano-connection based on C—C bonds to construct nanopolymers with a robust structure.

In fact, in addition to the thermodynamically reversible covalent bond strategy, other strategies, such as using non-covalent bonds to assist in inducing the formation of covalent bonds with the help of kinetic control, can also possibly minimize the disorderly cross-linking among molecules and make the bonding structure singular so as to achieve the requirement of the efficient nano-connection. But this also needs a corresponding conformational structure.

SUMMARY

In view of this, the present disclosure provides an organic nanogrids, nanopolymers thereof and preparation methods therefor in the context of efficient nano-connection. Compared with other organic closed-loop structures, the structural skeleton of the organic nanogrid is similar to a parallelogram, as shown in FIG. 1, wherein a pair of vertices have extensible and expandable properties. It can form a rigid polymer with regular structure through certain polymerization reaction. The method of synthesizing an organic nanogrid is to start from a precursor with appropriate geometric configuration, such as fluorene-like tertiary alcohol, and then to make the precursor undergo Friedel-Crafts cyclization reaction (as the basic model of nano-connection). This synthesis method has a high yield and few product types which are easy to separate. So it has important application prospects and good commercial development potential. On the other hand, this nano-connection can be used as a key way for constructing one-dimensional rigid organic nanopolymers. This connection mode can overcome shortcomings, such as the low molecular weight of the polymer, caused by the negative influence of steric hindrance in the traditional Suzuki or Yamamoto polymerization reaction. At the same time, it has a lot of advantages, such as transition metal-free catalysis, mild conditions, environmental friendliness and atomic economy, and is suitable for mass production of organic nanopolymers. On this basis, the present disclosure designs $A_2B_2$ monomers and can flexibly prepare one-dimensional nanopolymers with the help of nano-connection, thus laying a foundation for developing polymers with complex topologies.

The technical scheme of the present disclosure is as follows:

An organic nanogrid, with a general formula (I), is a centrally symmetric rigid closed-loop structure composed of two fluorene-like groups, of which one fluorene-like group belongs to a 9-phenyl fluorene derivative and can extend out to two connection sites, and the other fluorene group has a carbazole-like geometry;

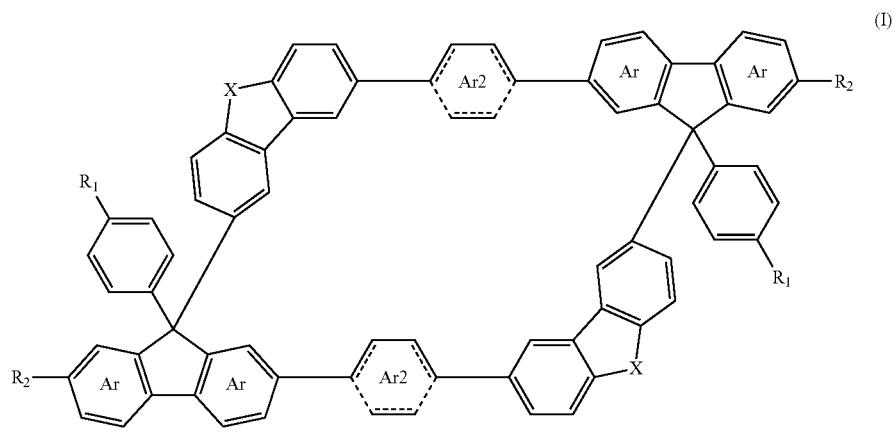

(I)

Wherein, $R_1$ includes: 1) linear chain type: hydrogen atom, alkane chain, alkoxy chain, and alkyl chain with halogen atoms introduced at the end; 2) branched chain type: tert-butyl group, and branched alkyl chain with oxygen atoms; n is a natural number from 1 to 10. Their specific structures are as follows:

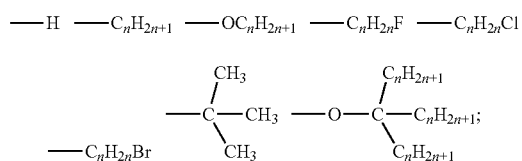

$R_2$ is a halogen or a photoelectrically active group. The above-mentioned photoelectrically active group includes: phenyl, pyrene, fluorene, nitrobenzene, benzocyano, and ethylcarbazole. Their specific structures are as follows:

X can be N atom, O atom or S atom, where the following structures can be introduced on N atoms:

is one of the following structures:

is one of the following structures:

A nanopolymer, with a general formula (II), is a polymer synthesized from some of the above-mentioned organic nanogrids through homopolymerization or copolymerization with photoelectric groups;

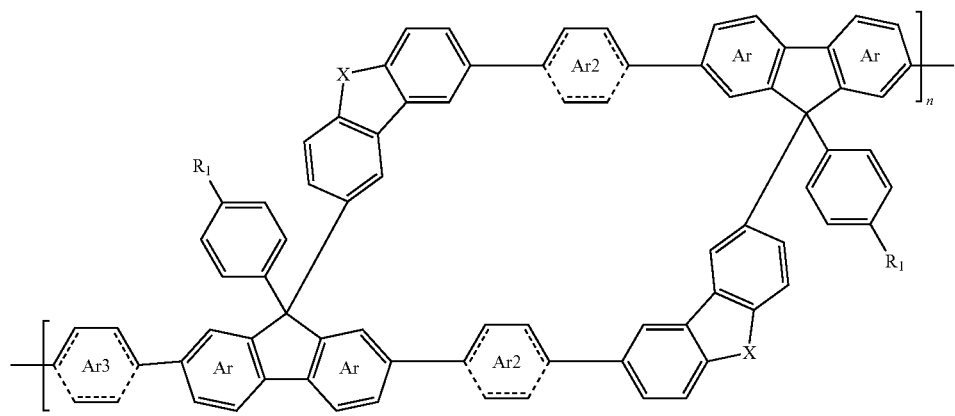

Wherein, n is a natural number from 1 to 10;

is one of the following structures:

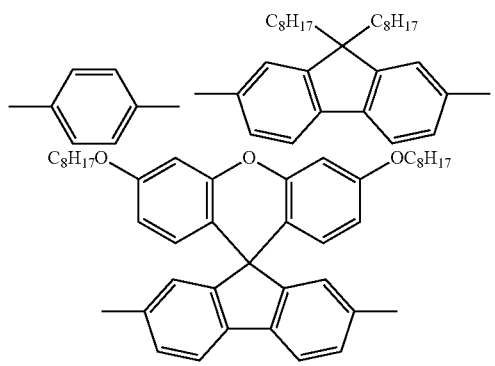

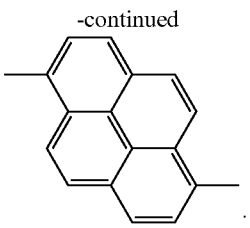

A method for preparing the organic nanogrid: a fluorene-like tertiary alcohol undergoes the Friedel-Crafts reaction in the presence of acid catalyst, and the fluorene-like tertiary alcohol undergoes intermolecular dehydration and cyclization to form the corresponding organic corner-cut grid. The reaction route is reaction formula (III).

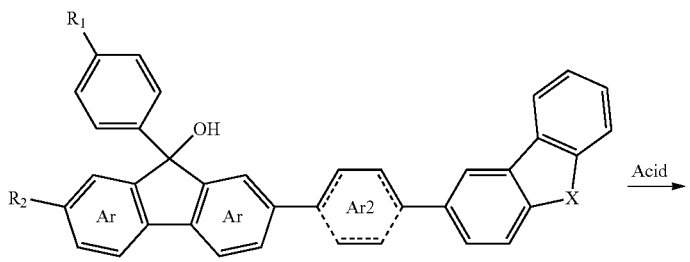

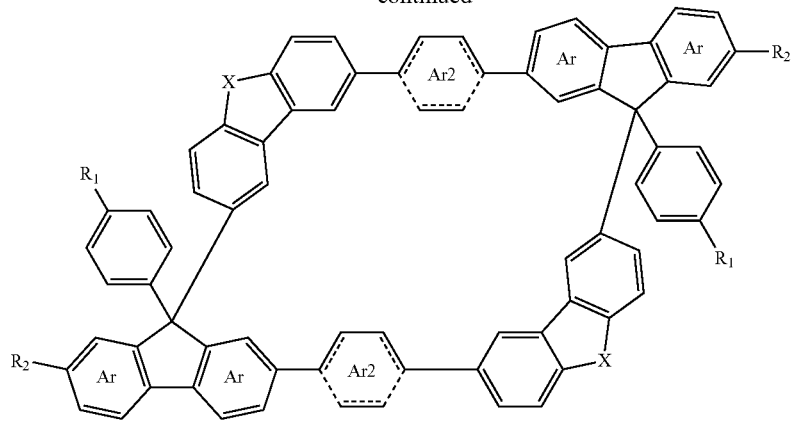
A method for preparing the nanopolymer: the corresponding organic nanopolymer is obtained from brominated organic nanogrids through the C—C bond coupling reaction. The reaction route is reaction formula (IV).
(IV)
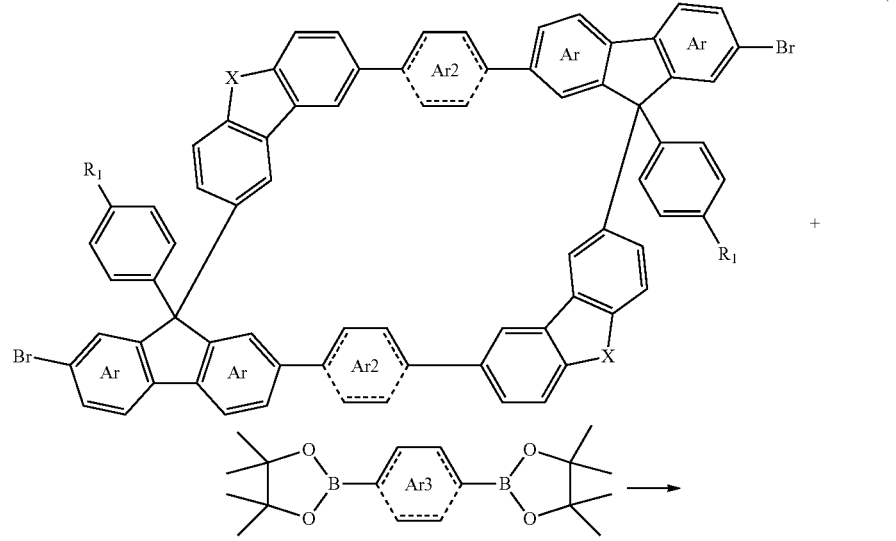
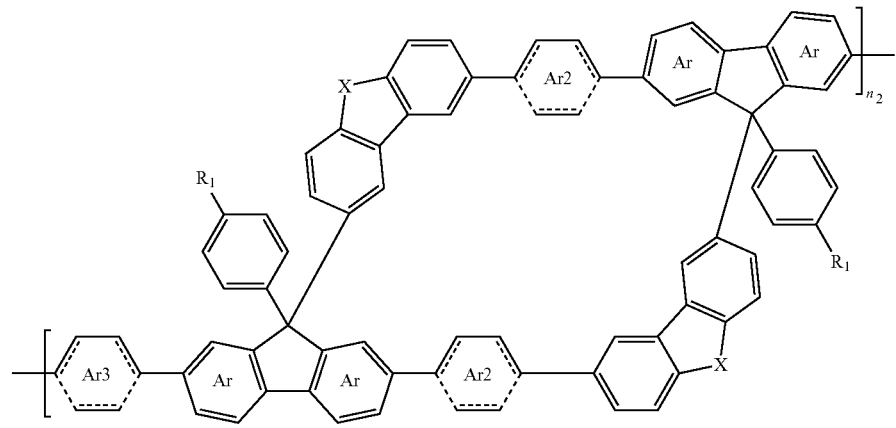

A method for preparing the nanopolymer: the organic nanopolymer is obtained from A₂B₂ polymerization monomers directly through the Friedel-Crafts polymerization. The reaction route is reaction formula (V).

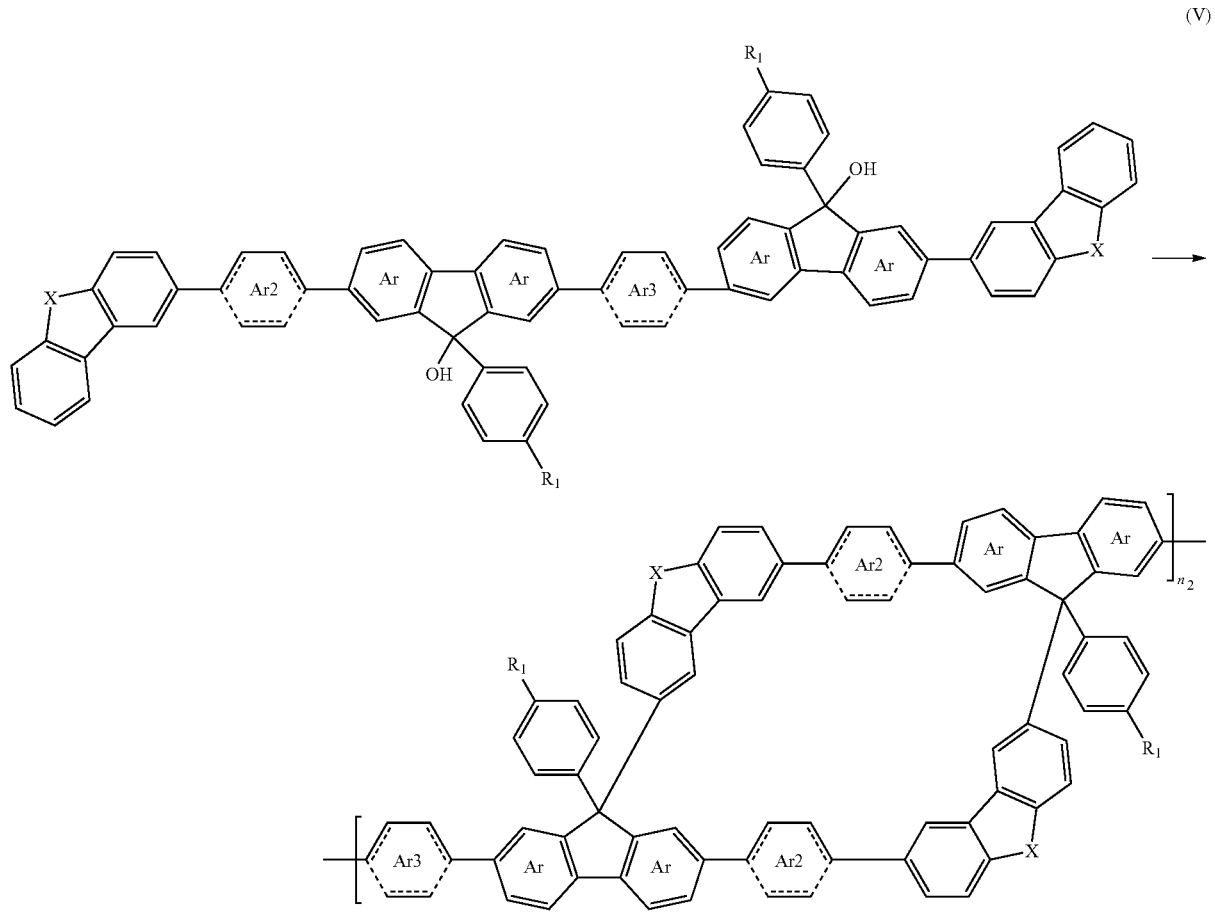

(V)

The present disclosure discloses an organic nanogrids, nanopolymers thereof and preparation methods therefor. It focuses on developing an efficient nano-connection mode, which has the following advantages compared with other nano-block/polymer connection modes:

(1) It inhibits the occurrence of cross-linked structures generated by disordered bonds by means of supramolecular assistance;

(2) It adopts the kinetically controlled supramolecular assistance mode to overcome the long time and harsh reaction conditions required by the traditional dynamic reversible process, so it can easily achieve industrial mass production;

(3) It overcomes shortcomings, such as the low molecular weight of the polymer, caused by the influence of steric hindrance in the traditional Suzuki or Yamamoto coupling polymerization reaction, so it facilitates the preparation of nanopolymers with a high molecular weight.

DESCRIPTION OF THE EMBODIMENTS

Figure 1:
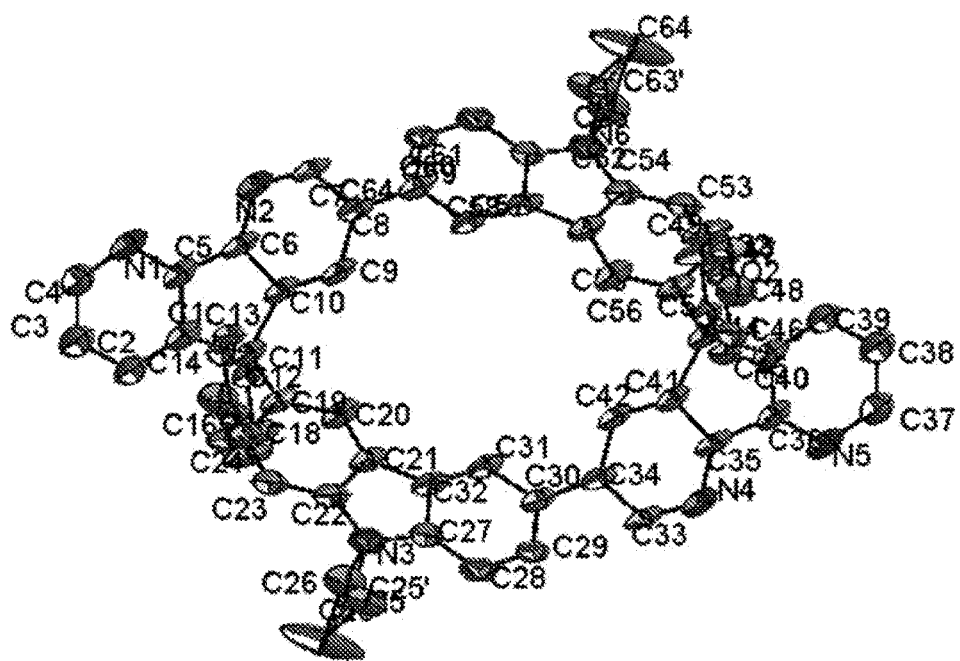
FIG. 1 shows the single crystal structure diagram of organic nanogrid 1e.

An organic nanogrid, with a general formula (I), is a centrally symmetric rigid closed-loop structure composed of two fluorene-like groups, of which one fluorene-like group belongs to a 9-phenyl fluorene derivative and can extend out to two connection sites, and the other fluorene group has a carbazole-like geometry;

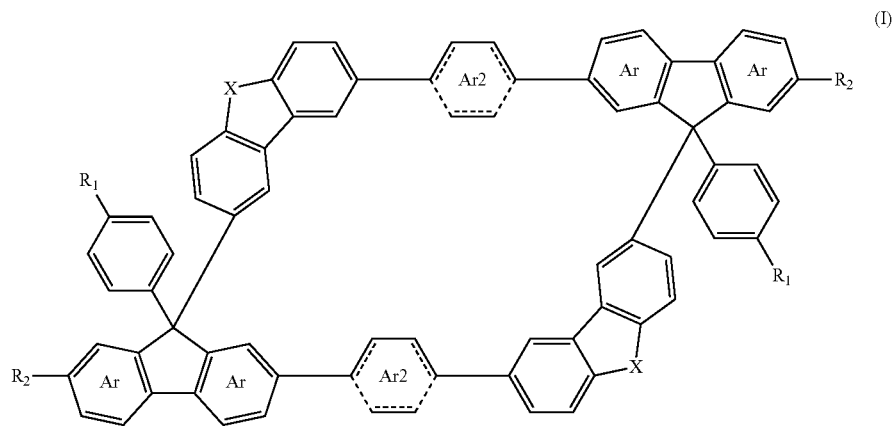

(I)

Wherein, $R_1$ includes: 1) linear chain type: hydrogen atom, alkane chain, alkoxy chain, and alkyl chain with halogen atoms introduced at the end; 2) branched chain type: tert-butyl group, and branched alkyl chain with oxygen atoms; n is a natural number from 1 to 10. Their specific structures are as follows:

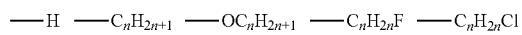

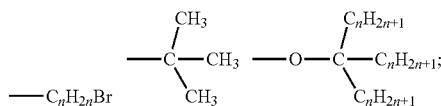

$R_2$ is a halogen or a photoelectrically active group. The above-mentioned photoelectrically active group includes: phenyl, pyrene, fluorene, nitrobenzene, benzocyano, and ethylcarbazole. Their specific structures are as follows:

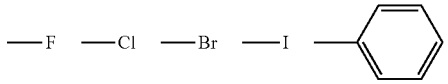

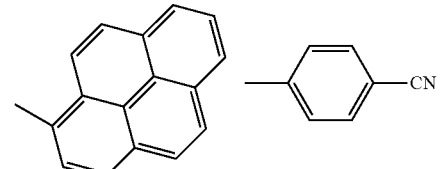

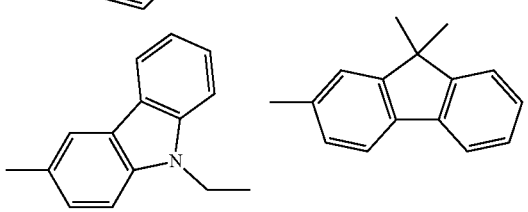

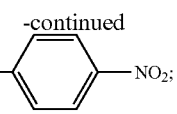

X can be N atom, O atom or S atom, where the following structures can be introduced on N atoms:

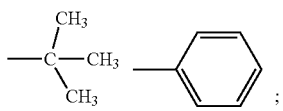

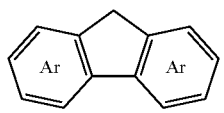

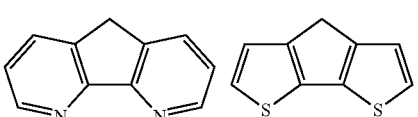

is one of the following structures:

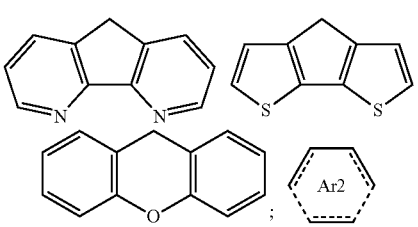

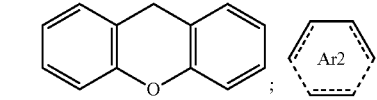

is one of the following structures:

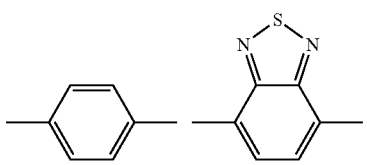

-continued

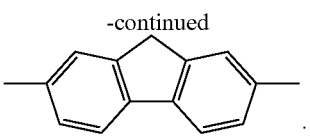

A nanopolymer, with a general formula (II), is a polymer synthesized from some of the above-mentioned organic nanogrids through homopolymerization or copolymerization with photoelectric groups;

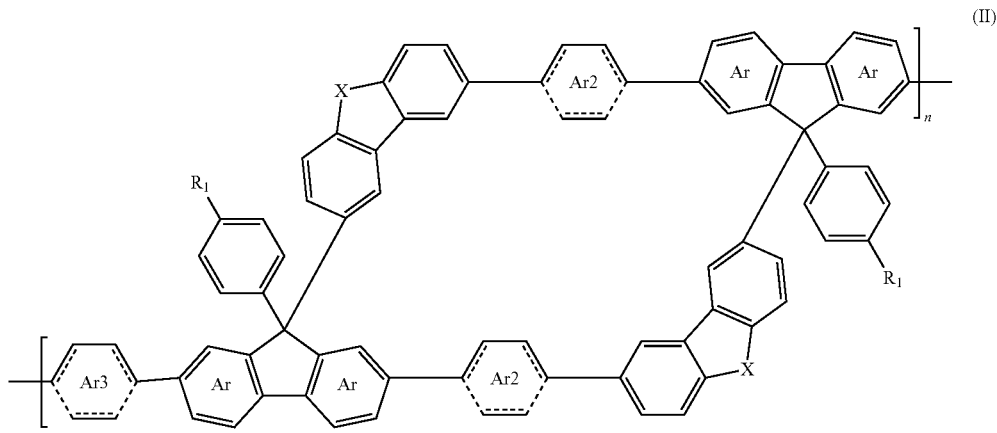

(II)

Wherein, n is a natural number from 1 to 10;

is one of the following structures:

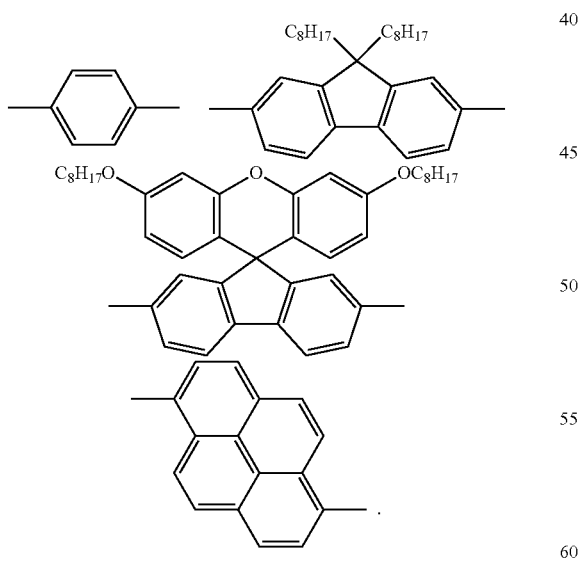

A method for preparing the organic nanogrid: a fluorene-like tertiary alcohol undergoes the Friedel-Crafts reaction in the presence of acid catalyst, and the fluorene-like tertiary alcohol undergoes intermolecular dehydration and cyclization to form the corresponding organic corner-cut grid. The reaction route is reaction formula (III).

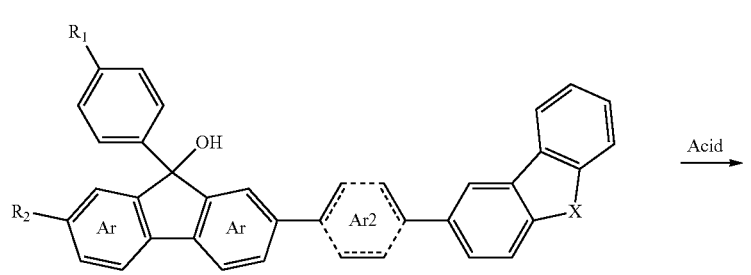

(III)

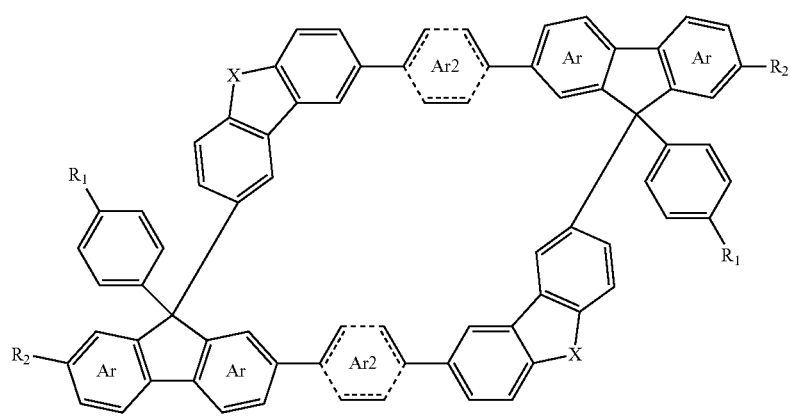

The synthesis strategies of the above-mentioned nanopolymer are: 1) one strategy is to obtain the corresponding organic nanopolymer from brominated organic nanogrids through the C—C bond coupling (Suzuki) reaction; 2) obtain the corresponding organic nanopolymer from $A_2B_2$ polymerization monomers directly through Friedel-Crafts polymerization.

The two polymerization strategies are shown in reaction formulas (IV) and (V), respectively.

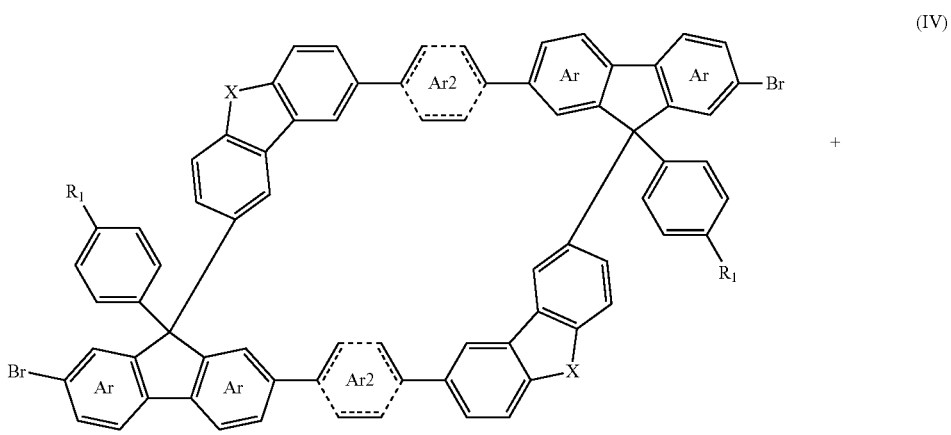

(IV)

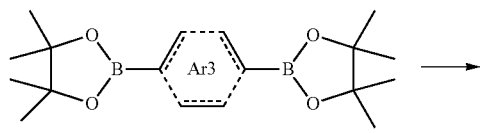

-continued
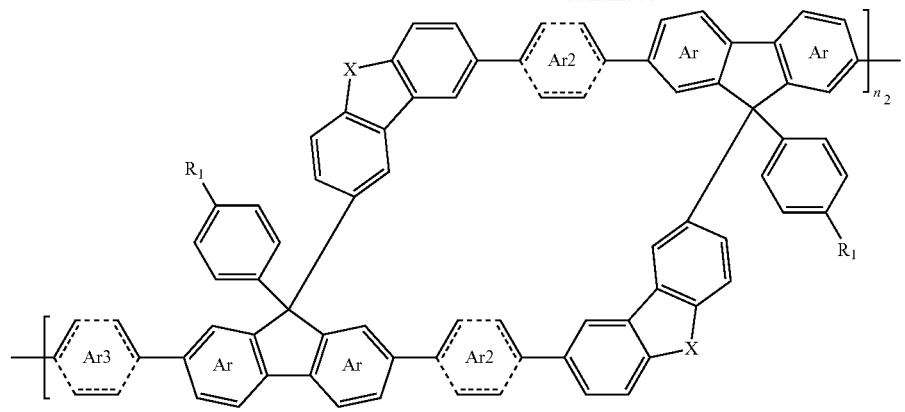
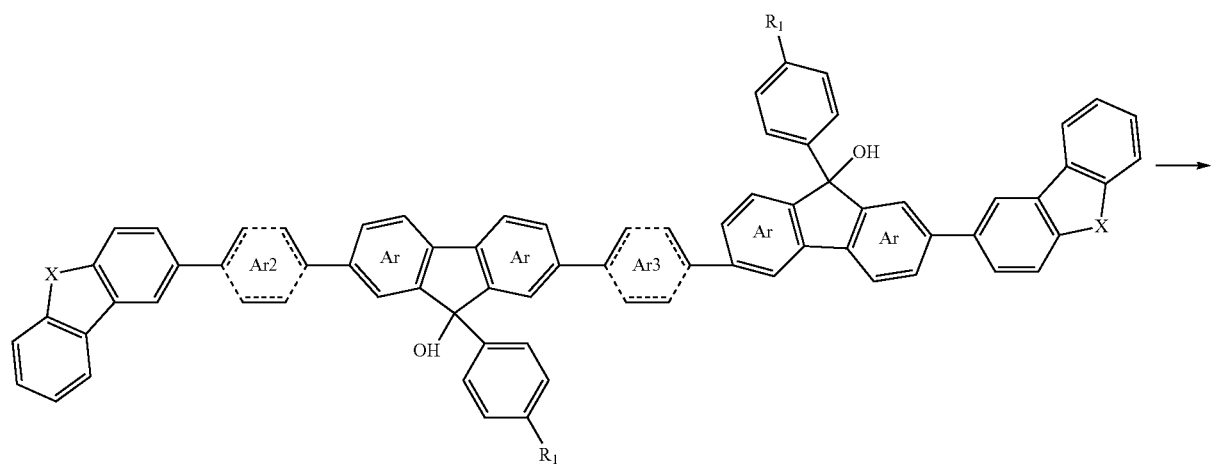
(V)
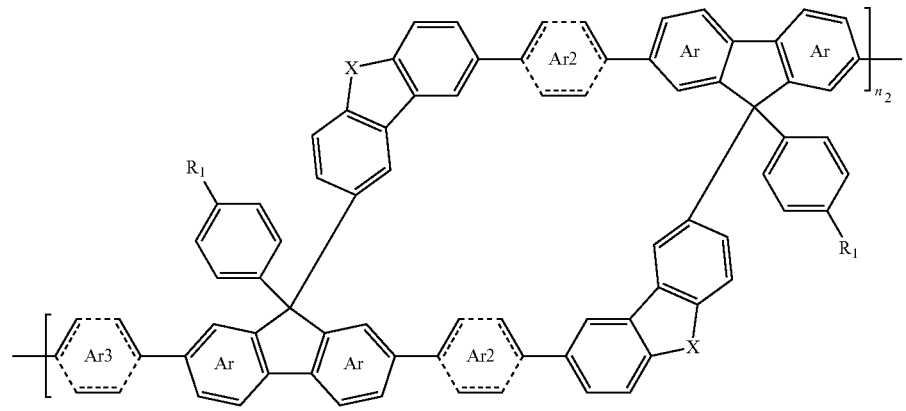

The technical scheme of the present disclosure will be further described below in conjunction with some embodiment cases. However, these embodiment cases do not limit the embodiment modes of the present disclosure. The present disclosure has many different embodiment modes, which are not limited to the above-mentioned content in this specification. Any schemes completed by any technician in the field without violating the spirit of the present disclosure shall fall within the scope of the present disclosure.

Embodiment Case 1: Preparation of Organic Nanogrids 1d and 1e

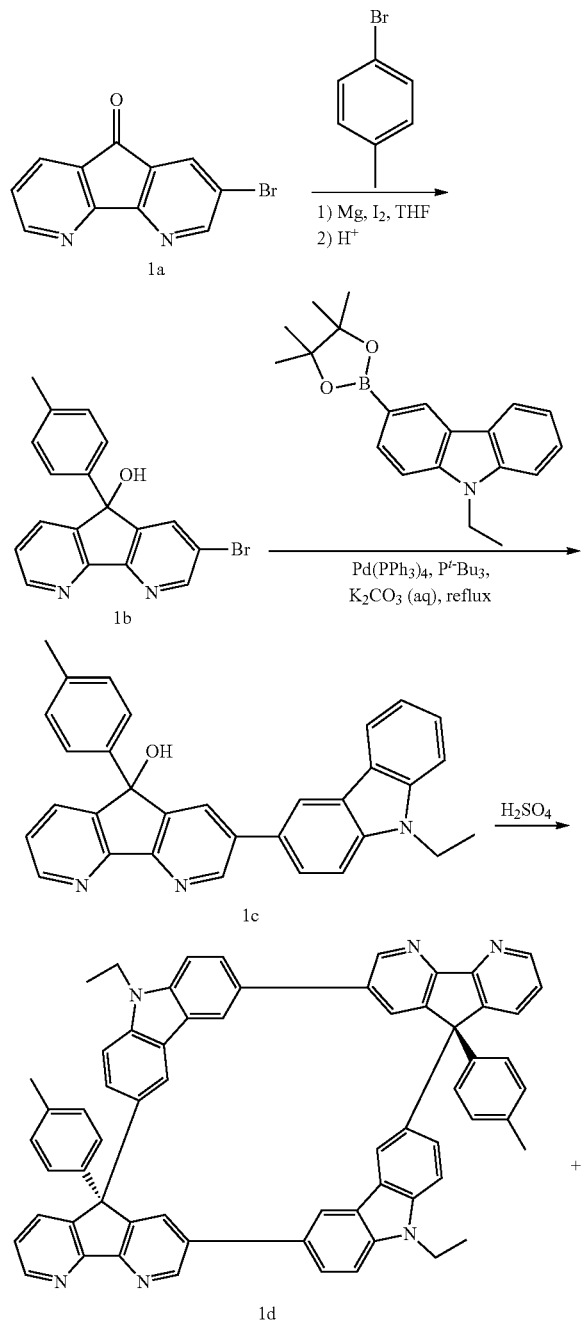

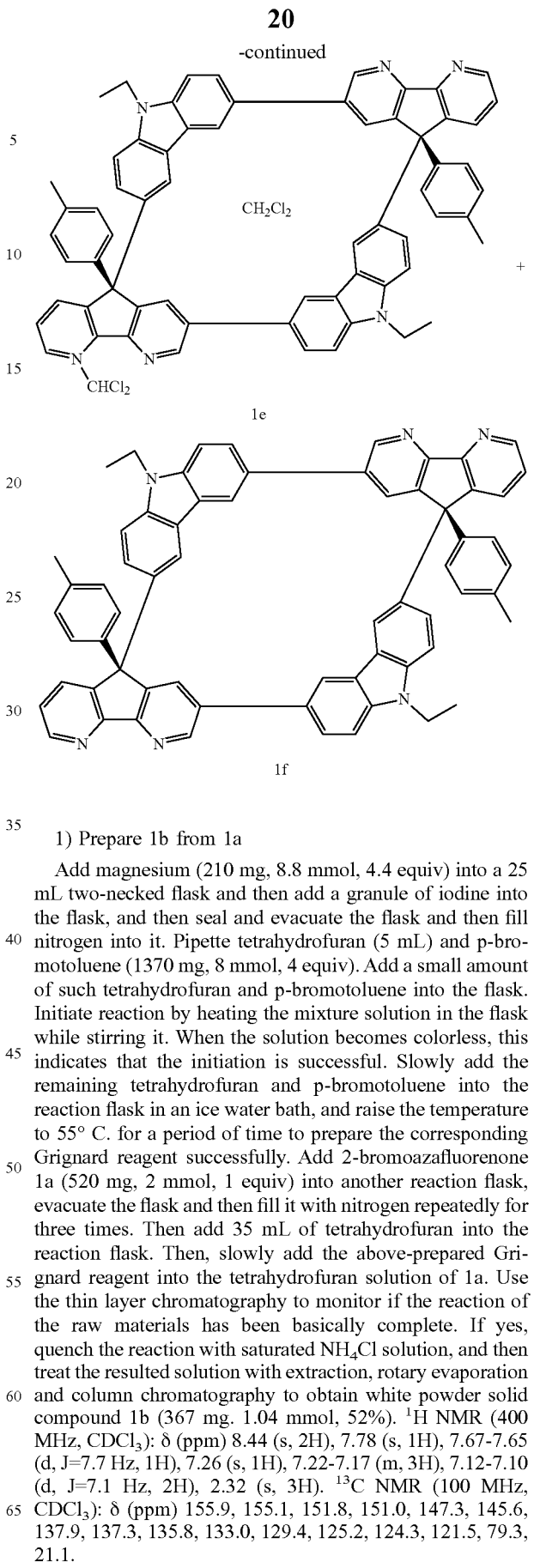

1) Prepare 1b from 1a

Add magnesium (210 mg, 8.8 mmol, 4.4 equiv) into a 25 mL two-necked flask and then add a granule of iodine into the flask, and then seal and evacuate the flask and then fill nitrogen into it. Pipette tetrahydrofuran (5 mL) and p-bromotoluene (1370 mg, 8 mmol, 4 equiv). Add a small amount of such tetrahydrofuran and p-bromotoluene into the flask. Initiate reaction by heating the mixture solution in the flask while stirring it. When the solution becomes colorless, this indicates that the initiation is successful. Slowly add the remaining tetrahydrofuran and p-bromotoluene into the reaction flask in an ice water bath, and raise the temperature to 55° C. for a period of time to prepare the corresponding Grignard reagent successfully. Add 2-bromoazafluorenone 1a (520 mg, 2 mmol, 1 equiv) into another reaction flask, evacuate the flask and then fill it with nitrogen repeatedly for three times. Then add 35 mL of tetrahydrofuran into the reaction flask. Then, slowly add the above-prepared Grignard reagent into the tetrahydrofuran solution of 1a. Use the thin layer chromatography to monitor if the reaction of the raw materials has been basically complete. If yes, quench the reaction with saturated $NH_4Cl$ solution, and then treat the resulted solution with extraction, rotary evaporation and column chromatography to obtain white powder solid compound 1b (367 mg. 1.04 mmol, 52%). $^1H$ NMR (400 MHz, $CDCl_3$): δ (ppm) 8.44 (s, 2H), 7.78 (s, 1H), 7.67-7.65 (d, J=7.7 Hz, 1H), 7.26 (s, 1H), 7.22-7.17 (m, 3H), 7.12-7.10 (d, J=7.1 Hz, 2H), 2.32 (s, 3H). $^{13}C$ NMR (100 MHz, $CDCl_3$): δ (ppm) 155.9, 155.1, 151.8, 151.0, 147.3, 145.6, 137.9, 137.3, 135.8, 133.0, 129.4, 125.2, 124.3, 121.5, 79.3, 21.1.

2) Prepare 1c from 1b

Add 1b (176 mg, 0.5 mmol, 1 equiv) and ethylcarbazole borate (193 mg, 0.6 mmol, 1.2 equiv) into a 25 mL reaction flask, and then seal and evacuate the flask and then fill it with nitrogen. Quickly add tetrakis (triphenylphosphine) palladium (0.06 g, 0.05 mmol, 0.1 equiv) into the flask under a nitrogen atmosphere, and then evacuate the flask once again and fill it with nitrogen again. Add tri-tert-butylphosphorus (0.37 mL, 0.1 mmol, 0.2 equiv, 0.1 wt % in toluene), toluene solvent (6 mL), and 0.5 M potassium carbonate aqueous solution (2.4 mL, 1.2 mmol, 2.4 equiv) into the reaction flask. In the dark, raise the reaction temperature to 110° C. and let the reaction go on for 6 h. Use the thin layer chromatography to monitor if the reaction of the raw materials has been basically complete. If yes, quench the reaction by adding water into it. Extract the resulted solution with dichloromethane, collect the organic phase, remove the solvent with rotary evaporation, and further separate and purify the organic phase with column chromatography to obtain white solid powder 1c (150 mg. 0.32 mmol. 63%). $^1$H NMR (400 MHz, CDCl$_3$): δ (ppm) 8.90 (s, 1H), 8.53-8.52 (d, J=4.8 Hz, 1H), 8.18 (s, 1H), 8.10-8.08 (d, J=7.8 Hz, 1H), 8.00 (s, 1H), 7.74-7.72 (d, J=8.1 Hz, 1H), 7.61-7.59 (d, J=8.4 Hz, 1H), 7.52-7.43 (s, 2H), 7.39-7.37 (d, J=7.8 Hz, 1H), 7.34-7.32 (d, J=8.0 Hz, 2H), 7.27-7.23 (m, 3H), 7.20-7.17 (dd, J=6.8, 5.8 Hz, 1H), 7.13-7.11 (d, J=7.8 Hz, 1H), 4.27-4.22 (q, J=6.4 Hz, 1H), 2.31 (s, 3H), 1.40-1.37 (t, J=7.2 Hz, 1H).

3) Preparation of 1d, 1e and 1f (organic nanogrids) from 1c

Figure 4:
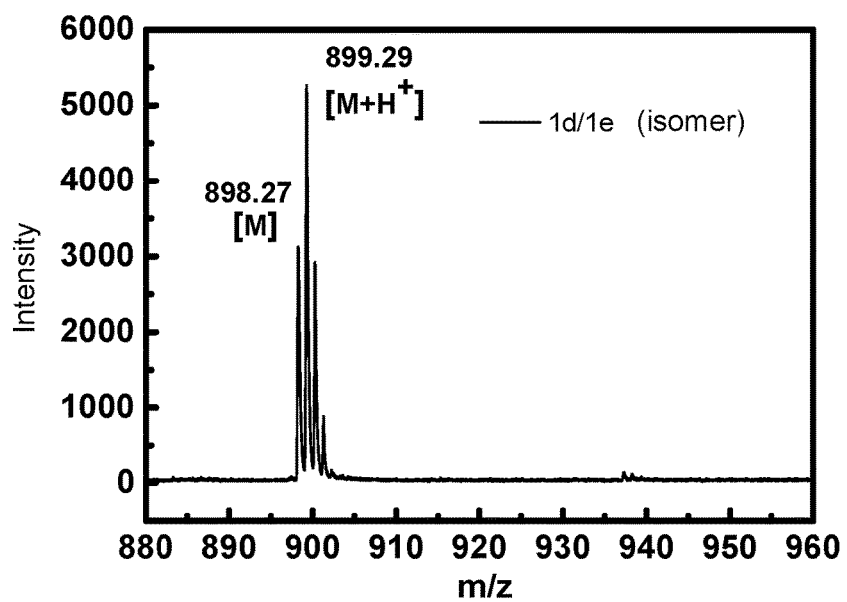
FIG. 4 shows the time-of-flight mass spectrum of organic nanogrid 1d/1e (a pair of isomers)

Add 1c (46 mg, 0.1 mmol, 1 equiv) into a small reaction flask, and then add 5 mL of dichloromethane into the flask. After stirring the resulted solution for 30 min, add concentrated sulfuric acid (1 mL) into it quickly. Use the thin layer chromatography to monitor if the reaction of the raw materials has been basically complete. If yes, add potassium hydroxide aqueous solution to quench the reaction. Extract the resulted solution with dichloromethane, collect the organic phase, remove the solvent with rotary evaporation, and further separate and purify the organic phase with column chromatography to obtain light yellow solid powder 1d, 1e and 1f. From the time-of-flight mass spectrogram in FIG. 4, it can be found that the molecular weight of the product in this reaction solution is 898.27 and 899.29, which can correspond to the intrinsic molecular weight of 1d/1e and the molecular weight after protonation, respectively, indicating that only a two-grid product exists in the reaction system.

1d: (9 mg, 0.01 mmol. 20%) 8.95-8.94 (d, J=1.8 Hz, 2H), 8.80-8.78 (dd, J=4.8, 1.3 Hz, 2H), 8.58 (d, J=1.6 Hz, 2H), 8.29-8.27 (dd, J=9.2, 1.6 Hz, 4H), 8.01-7.98 (dd, J=7.7, 1.3 Hz, 2H), 7.74-7.71 (dd, J=8.4, 1.6 Hz, 2H), 7.62-7.59 (dd, J=8.7, 1.8 Hz, 2H), 7.52-7.49 (dd, J=8.5 Hz, 2H), 7.38-7.35 (m, 4H), 6.91-6.89 (d, J=8.2 Hz, 4H), 6.78-6.75 (d, J=8.3 Hz, 4H), 4.43-4.39 (m, 4H), 2.19 (s, 6H), 1.48-1.45 (t, J=7.0 Hz, 6H).

Figure 2:
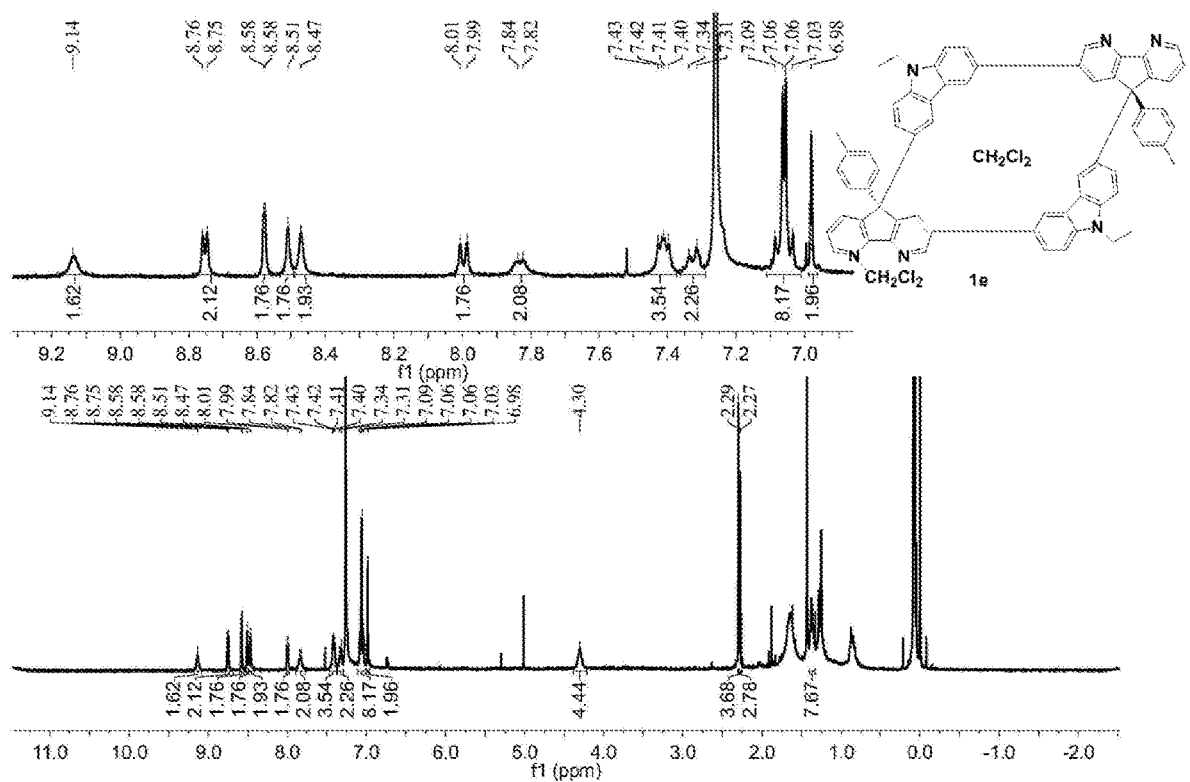
FIG. 2 shows the 1H-NMR of organic nanogrid 1e.

1e: (6.7 mg, 0.01075 mmol. 15%) $^1$H NMR (400 MHz, CDCl$_3$): δ (ppm) 9.14 (s, 2H), 8.76-8.75 (d, J=5.8 Hz, 2H), 8.58 (d, J=1.5 Hz, 2H), 8.51 (s, 2H), 8.47 (s, 2H), 8.01-7.99 (d, J=7.9 Hz, 2H), 7.84-7.82 (d, J=6.1 Hz, 2H), 7.43-7.40 (dd, J=7.4 Hz, 4.6 Hz, 4H), 7.34-7.31 (d, J=9.5 Hz, 2H), 7.09-7.03 (m, 8H), 6.98 (s, 2H), 4.30 (m, 4H), 2.29 (s, 3H), 2.27 (s, 3H). The single crystal structure of this compound is shown in FIG. 1 (the pores in the center of the skeleton of the compound appear square, so the compound is called organic nanogrid). The 1H-NMR (the full spectrum and the area where the aromatic zone is enlarged) is shown in FIG. 2 for details.

Figure 3:
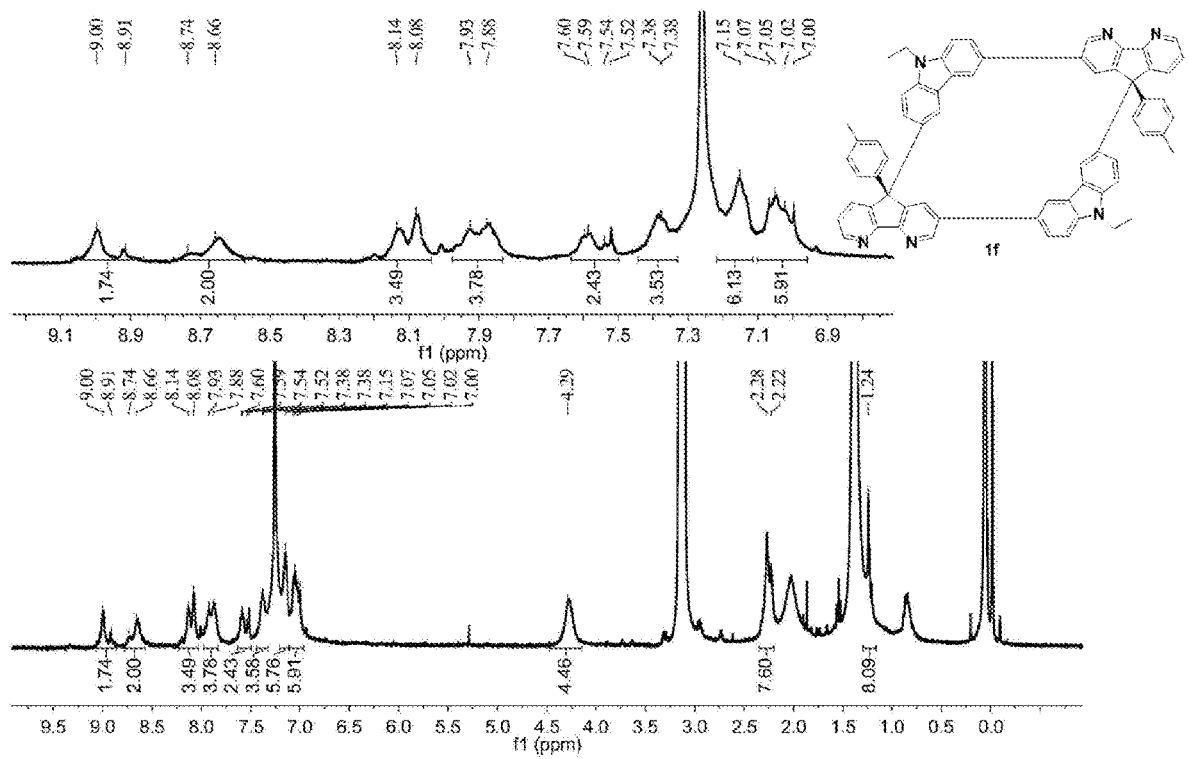
FIG. 3 shows the 1H-NMR of organic nanogrid 1f

1f: (34 mg. 0.0375 mmol. 75%). $^1$H NMR (400 MHz, CDCl$_3$): δ (ppm) 9.00-8.91 (2H), 8.74-8.66 (2H), 8.14-8.08 (4H), 7.93-7.88 (4H), 7.60-7.52 (2H), 7.38 (4H), 7.25-7.15 (6H), 7.05-7.00 (6H), 4.29 (4H), 2.28-2.22 (6H), 1.24 (6H). (Note: Probably due to the paramagnetism caused by the syntropy of two azafluorenes, the nuclear magnetic signal peaks are not separated.) Its 1H-NMR (the full spectrum and the area where the aromatic zone is enlarged) is shown in FIG. 3 for details.

Embodiment Case 2: Preparation of Organic Nanogrids 2d and 2e

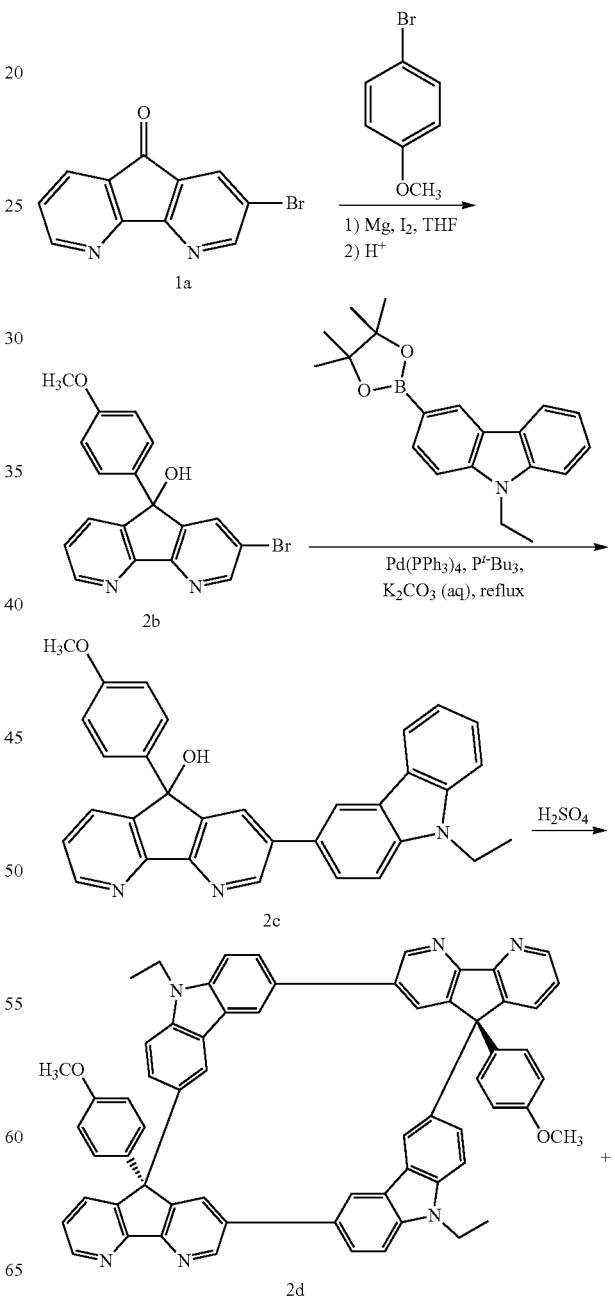

2d

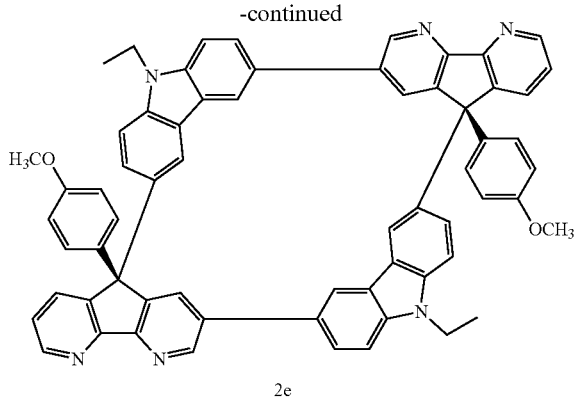

2e

1) Prepare 2b from 1a

Add magnesium (210 mg, 8.8 mmol, 4.4 equiv) into a 25 mL two-necked flask and then add a granule of iodine into the flask, and then seal and evacuate the flask and then fill nitrogen into it. Pipette tetrahydrofuran (5 mL) and p-bromoanisole (1240 mg, 8 mmol, 4 equiv). Add a small amount of such tetrahydrofuran and p-bromoanisole into the flask. Initiate reaction by heating the mixture solution in the flask while stirring it. When the solution becomes colorless, this indicates that the initiation is successful. Slowly add the remaining tetrahydrofuran and p-bromoanisole into the reaction flask in an ice water bath, and raise the temperature to 55° C. for a period of time to prepare the corresponding Grignard reagent successfully. Add 2-bromoazafluorenone 1a (520 mg, 2 mmol, 1 equiv) into another reaction flask, evacuate the flask and then fill it with nitrogen repeatedly for three times. Then add 35 mL of tetrahydrofuran into the reaction flask. Then, slowly add the above-prepared Grignard reagent into the tetrahydrofuran solution of 1a. Use the thin layer chromatography to monitor if the reaction of the raw materials has been basically complete. If yes, quench the reaction with saturated NH4Cl solution, and then treat the resulted solution with extraction, rotary evaporation and column chromatography to obtain white powder solid compound 2b (141 mg. 0.35 mmol. 71%). $^1$H NMR (400 MHz, CDCl$_3$): δ (ppm) 8.26-8.25 (m, 2H), 7.76-7.75 (d, J=2.0 Hz, 1H), 7.76-7.72 (dd, J=7.7 Hz, 1.3 Hz, 1H), 7.24-7.22 (dd, J=8.8 Hz, 2H), 7.13-7.10 (dd, J=7.6 Hz, 4.9 Hz, 1H), 6.81-6.79 (d, J=8.8 Hz, 2H), 5.59 (s, 1H). $^{13}$C NMR (100 MHz, CDCl$_3$): δ (ppm) 159.3, 155.6, 154.9, 151.5, 150.7, 147.6, 145.9, 135.7, 133.0, 132.5, 126.6, 124.2, 121.4, 114.0, 78.9, 55.3.

2) Prepare 2c from 2b

Add 2b (184 mg, 0.5 mmol, 1 equiv) and ethylcarbazole borate (193 mg, 0.6 mmol, 1.2 equiv) into a 25 mL reaction flask, and then seal and evacuate the flask and then fill it with nitrogen. Quickly add tetrakis (triphenylphosphine)palladium (0.06 g, 0.05 mmol, 0.1 equiv) into the flask under a nitrogen atmosphere, and then evacuate the flask once again and fill it with nitrogen again. Add tri-tert-butylphosphorus (0.37 mL, 0.1 mmol, 0.2 equiv, 0.1 wt % in toluene), toluene solvent (6 mL), and 0.5 M potassium carbonate aqueous solution (2.4 mL, 1.2 mmol, 2.4 equiv) into the reaction flask. In the dark, raise the reaction temperature to 110° C. and let the reaction go on for 6 h. Use the thin layer chromatography to monitor if the reaction of the raw materials has been basically complete. If yes, quench the reaction by adding water into it. Extract the resulted solution with dichloromethane, collect the organic phase, remove the solvent with rotary evaporation, and further separate and purify the organic phase with column chromatography to obtain white solid powder 2c (141 mg. 0.35 mmol. 71%). $^1$H NMR (400 MHz, CDCl$_3$): δ (ppm) 8.75 (d, J=1.2 Hz, 1H), 8.39-8.38 (d, J=4.3 Hz, 1H), 8.07 (s, 1H), 8.02-8.01 (d, J=7.6 Hz, 1H), 7.94 (d, J=1.5 Hz, 1H), 7.68-7.66 (d, J=7.5 Hz, 1H), 7.53-7.51 (d, J=7.9 Hz, 1H), 7.47-7.45 (d, J=8.0 Hz, 1H), 7.37-7.32 (m, 3H), 7.23-7.20 (t, J=7.4 Hz, 1H), 7.19-7.17 (d, J=8.3 Hz, 1H), 7.08-7.05 (dd, J=7.6 Hz, 4.9 Hz, 1H), 6.82-6.80 (d, J=8.6 Hz, 2H), 4.11-4.08 (m, 2H), 3.74 (s, 3H), 1.37-1.31 (m, 3H).

3) Preparation of 2d and 2e (Organic Nanogrids) from 2c

Figure 7:
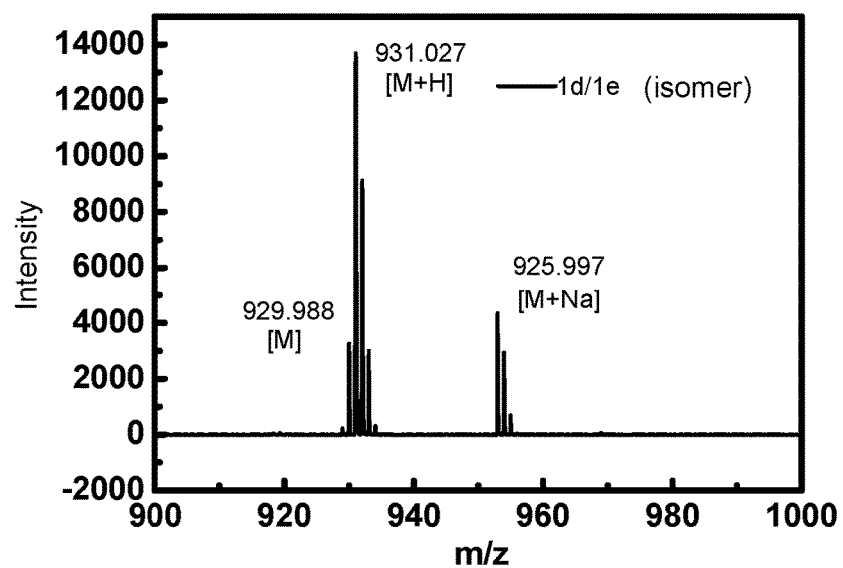
FIG. 7 shows the time-of-flight mass spectrum of organic nanogrid 2d/2e (a pair of isomers)

Add 2c (48 mg, 0.1 mmol, 1 equiv) into a small reaction flask, and then add 5 mL of dichloromethane into the flask. After stirring the resulted solution for 30 min, add concentrated sulfuric acid (1 mL) into it quickly. Use the thin layer chromatography to monitor if the reaction of the raw materials has been basically complete. If yes, add potassium hydroxide aqueous solution to quench the reaction. Extract the resulted solution with dichloromethane, collect the organic phase, remove the solvent with rotary evaporation, and further separate and purify the organic phase with column chromatography to obtain light yellow solid powder 2d and 2e. From the time-of-flight mass spectrogram in FIG. 7, it can be found that basically only a two-grid product exists in the reaction system.

Figure 5:
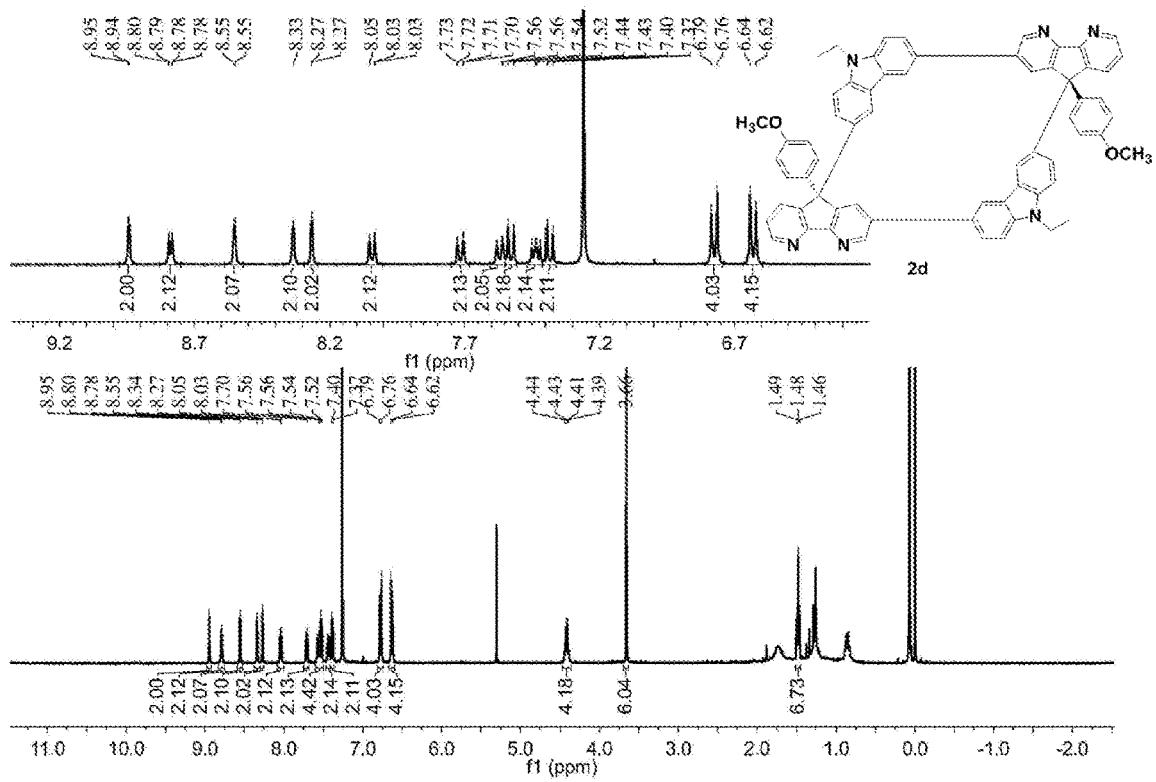
FIG. 5 shows the 1H-NMR of organic nanogrid 2d.

2d: (9 mg, 0.01 mmol. 20%) $^1$H NMR (400 MHz, CDCl$_3$): δ (ppm) 9.14 (s, 2H), 8.76-8.75 (d, J=5.8 Hz, 2H), 8.58 (d, J=1.5 Hz, 2H), 8.51 (s, 2H), 8.47 (s, 2H), 8.01-7.99 (d, J=7.9 Hz, 2H), 7.84-7.82 (d, J=6.1 Hz, 2H), 7.43-7.40 (dd, J=7.4 Hz, 4.6 Hz, 4H), 7.34-7.31 (d, J=9.5 Hz, 2H), 7.09-7.03 (m, 8H), 6.98 (s, 2H), 4.30 (m, 4H), 2.29 (s, 3H), 2.27 (s, 3H). Its 1H-NMR (the full spectrum and the area where the aromatic zone is enlarged) is shown in FIG. 5 for details.

Figure 6:
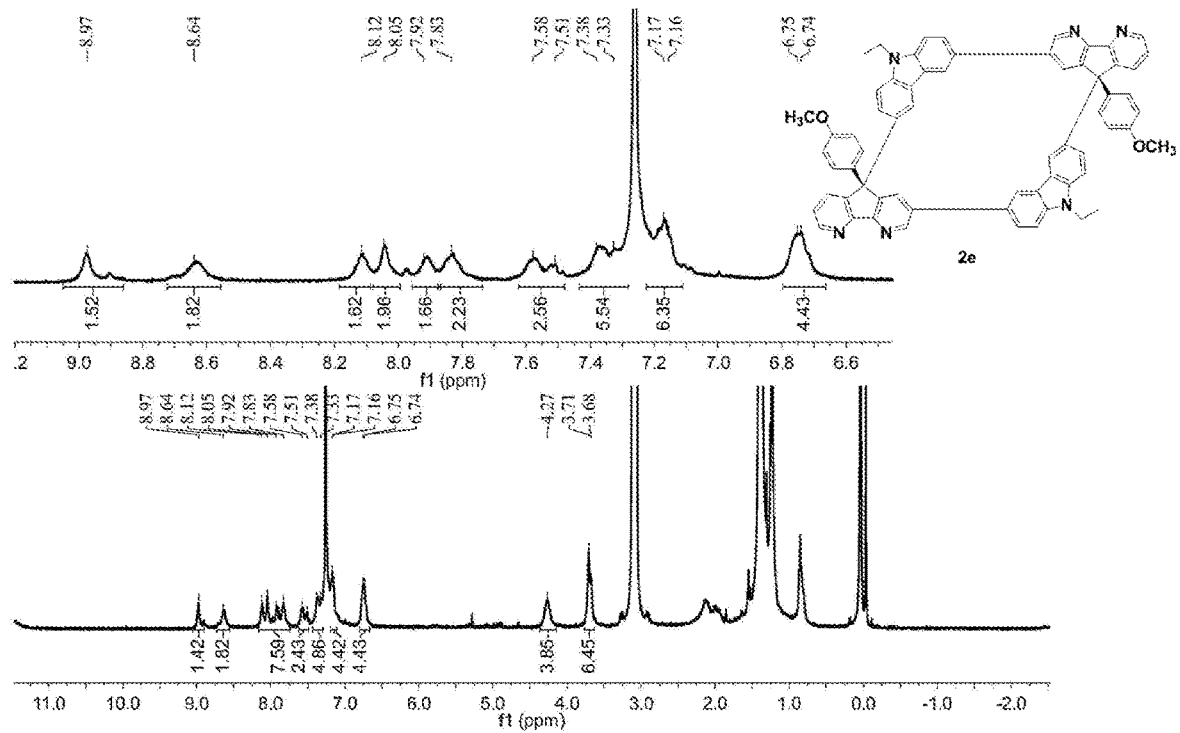
FIG. 6 shows the 1H-NMR of organic nanogrid 2e.

2e: (34 mg. 0.0375 mmol. 75%). $^1$H NMR (400 MHz, CDCl$_3$): δ (ppm) 9.00-8.91 (2H), 8.74-8.66 (2H), 8.14-8.08 (4H), 7.93-7.88 (4H), 7.60-7.52 (2H), 7.38 (4H), 7.25-7.15 (6H), 7.05-7.00 (6H), 4.29 (4H), 2.28-2.22 (6H), 1.24 (6H). (Note: Probably due to the paramagnetism caused by the syntropy of two azafluorenes, the nuclear magnetic signal peaks are not separated.) Its 1H-NMR (the full spectrum and the area where the aromatic zone is enlarged) is shown in FIG. 6 for details.

Embodiment Case 3: Preparation of Organic Nanogrids 3d and 3e

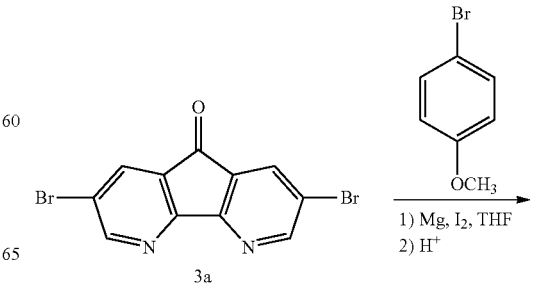

3a

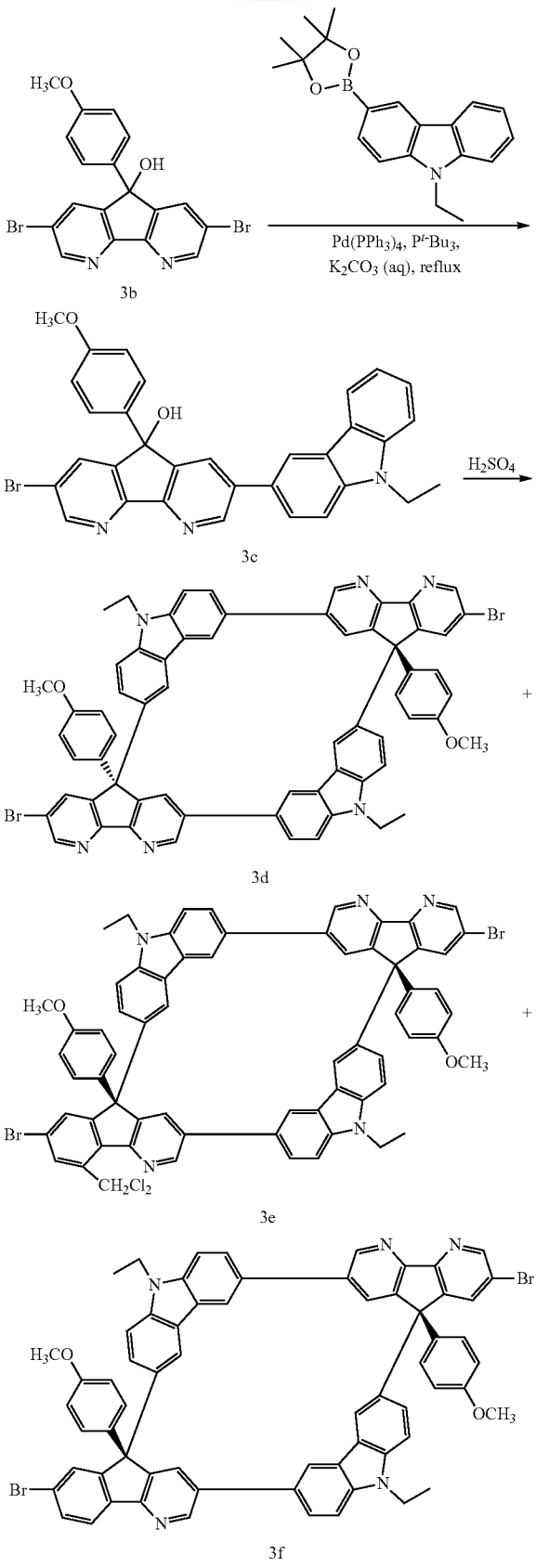

1) Prepare 3b from 3a

Add magnesium (560 mg, 23.1 mmol, 3.3 equiv) into a 50 mL two-necked flask and then add a granule of iodine into the flask, and then seal and evacuate the flask and then fill nitrogen into it. Pipette tetrahydrofuran (12 mL) and p-bromoanisole (2.50 mL, 21 mmol, 3 equiv). Add a small amount of such tetrahydrofuran and p-bromoanisole into the flask. Initiate reaction by heating the mixture solution in the flask while stirring it. When the solution becomes colorless, this indicates that the initiation is successful. Slowly add the remaining tetrahydrofuran and p-bromoanisole into the reaction flask in an ice water bath, and raise the temperature to 55° C. for a period of time to prepare the corresponding Grignard reagent successfully. Add 2,7-dibromo-azafluorenone 3a (2380 mg, 7 mmol, 1 equiv) into another reaction flask, evacuate the flask and then fill it with nitrogen repeatedly for three times. Then add 100 mL of tetrahydrofuran into the reaction flask. Then, slowly add the above-prepared Grignard reagent into the tetrahydrofuran solution of 3a. Use the thin layer chromatography to monitor if the reaction of the raw materials has been basically complete. If yes, quench the reaction with saturated NH4Cl solution, and then treat the resulted solution with extraction, rotary evaporation and column chromatography to obtain white powder solid compound 3b (1912 mg. 4.27 mmol. Yield: 61%). $^1$H NMR (400 MHz, CDCl$_3$): δ (ppm) $^1$H NMR (400 MHz, CDCl$_3$): δ (ppm) 8.45-8.44 (d, J=2.0 Hz, 2H), 7.78-7.77 (d, J=2.0 Hz, 2H), 7.25-7.23 (d, J=8.8 Hz, 2H), 6.85-6.83 (d, J=8.8 Hz, 2H), 4.61 (s, 1H), 3.79 (s, 3H). $^{13}$C NMR (100 MHz, CDCl$_3$): δ (ppm) 159.6, 154.3, 152.2, 147.1, 135.8, 131.4, 126.5, 121.9, 114.2, 78.9, 55.3. HRMS: m/z calcd for [M+H$^+$] $C_{18}H_{13}O_2N_2Br_2$: 446.9338; found: 446.9336.

2) Prepare 3c from 3b

Add 3b (1350 mg, 3 mmol, 1 equiv) and ethylcarbazole borate (960 mg, 3 mmol, 1 equiv) into a 25 mL reaction flask, and then seal and evacuate the flask and then fill it with nitrogen. Quickly add tetrakis(triphenylphosphine)palladium (360 mg, 0.3 mmol, 0.1 equiv) into the flask under a nitrogen atmosphere, and then evacuate the flask once again and fill it with nitrogen again. Add tri-tert-butylphosphorus (2.9 mL, 1.2 mmol, 0.4 equiv, 0.1 wt % in toluene), toluene solvent (6 mL), and 2 M potassium carbonate aqueous solution (3 mL, 6 mmol, 2 equiv) into the reaction flask. In the dark, raise the reaction temperature to 110° C. and let the reaction go on for 6 h. Use the thin layer chromatography to monitor if the reaction of the raw materials has been basically complete. If yes, quench the reaction by adding water into it. Extract the resulted solution with dichloromethane, collect the organic phase, remove the solvent with rotary evaporation, and further separate and purify the organic phase with column chromatography to obtain white solid powder 3c (710 mg. 1.26 mmol. Yield: 42%). $^1$H NMR (400 MHz, CDCl$_3$): δ (ppm) $^1$H NMR (400 MHz, CDCl$_3$): δ (ppm) 8.77 (d, J=2.1 Hz, 1H), 8.46 (d, J=2.1 Hz, 1H), 7.98 (d, J=1.3 Hz, 1H), 7.97-7.95 (d, J=7.9 Hz, 1H), 7.90 (d, J=1.9 Hz, 1H), 7.79 (d, J=1.9 Hz, 1H), 7.50-7.43 (m, 2H), 7.36-7.33 (d, J=8.7 Hz, 2H), 7.30-7.28 (d, J=8.9 Hz, 1H), 7.22-7.18 (t, J=7.4 Hz, 1H), 7.12-7.10 (d, J=8.9 Hz, 1H), 6.84-6.82 (d, J=8.8 Hz, 2H), 4.91 (s, 1H), 4.03-3.96 (m, 2H), 3.76 (s, 3H), 1.70 (s, 3H). $^{13}$C NMR (100 MHz, CDCl$_3$): δ (ppm) 159.4, 155.1, 153.7, 151.9, 150.0, 147.5, 145.8, 140.2, 139.6, 138.5, 135.4, 132.4, 130.7, 127.4, 126.7, 126.0, 124.5, 123.4, 122.7, 121.1, 120.5, 119.1, 118.8, 114.0, 108.7, 108.5, 79.1, 55.3, 37.3, 13.7. HRMS: m/z calcd for [M+H$^+$] $C_{32}H_{25}O_2N_3Br_1$: 562.1125; found: 562.1124.

3) Preparation of 3d, 3e and 3f (Organic Nanogrids) from 3c

Add 3c (150 mg, 0.27 mol, 1 equiv) into a small reaction flask, and then add 0.9 mL of dichloromethane into the flask. After stirring the resulted solution for 30 min, add concentrated sulfuric acid (0.22 mL, 4.05 mmol, 15 equiv) into it quickly. Use the thin layer chromatography to monitor if the reaction of the raw materials has been basically complete. If yes, add potassium hydroxide aqueous solution to quench the reaction. Extract the resulted solution with dichloromethane, collect the organic phase, remove the solvent with rotary evaporation, and further separate and purify the organic phase with column chromatography to obtain light yellow solid powder 3d, 3e and 3f.

Figure 8:
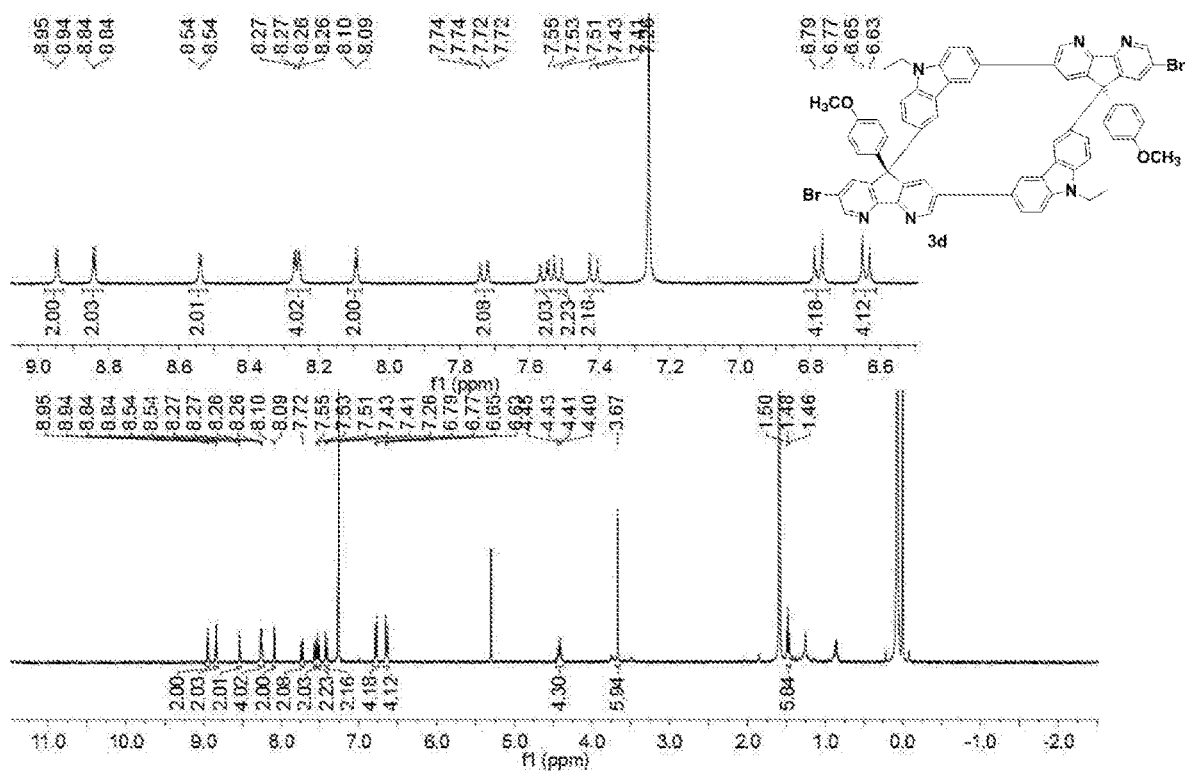
FIG. 8 shows the 1H-NMR of organic nanogrid 3d.

3d (35 mg, 0.032 mmol. Yield: 24%) $^1$H NMR (400 MHz, CDCl$_3$): δ (ppm) 8.95-8.94 (d, J=1.9 Hz, 2H), 8.84 (d, J=2.0 Hz, 2H), 8.54 (d, J=2.0 Hz, 2H), 8.27-8.26 (dd, J=4.2 Hz, 1.5 Hz, 4H), 8.10-8.09 (d, J=2.2 Hz, 2H), 7.74-7.72 (dd, J=8.5 Hz, 1.9 Hz, 2H), 7.57-7.55 (dd, J=8.7 Hz, 1.9 Hz, 2H), 7.53-7.51 (d, J=8.4 Hz, 2H), 7.43-7.41 (d, J=8.8 Hz, 2H), 6.79-6.77 (d, J=8.9 Hz, 4H), 6.65-6.63 (d, J=8.9 Hz, 4H). 4.45-4.40 (m, 4H), 3.67 (s, 6H), 1.50-1.46 (m, 3H). HRMS: m/z calcd for [M+H$^+$] C$_{64}$H$_{45}$O$_2$N$_6$Br$_2$: 1087.1965; found: 1087.1964. Its 1H-NMR (the full spectrum and the area where the aromatic zone is enlarged) is shown in FIG. 8 for details.

Figure 9:
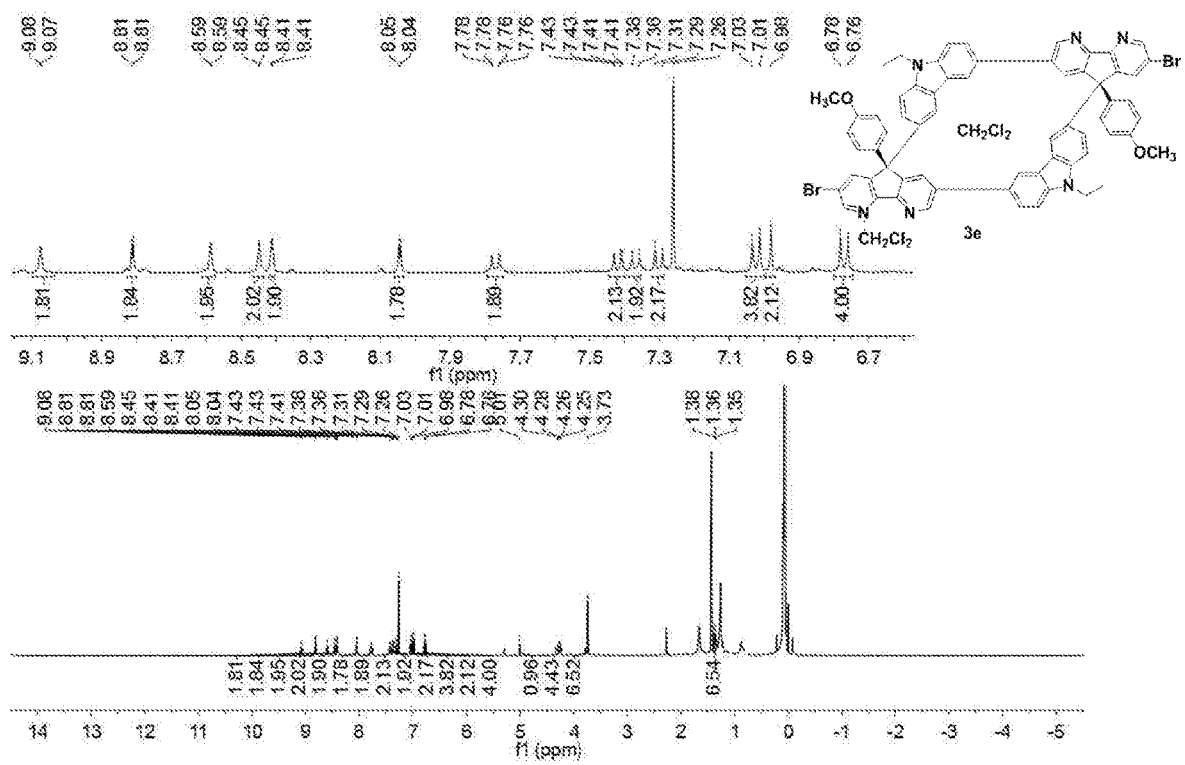
FIG. 9 shows the 1H-NMR of organic nanogrid 3e.

3e (18 mg, 0.017 mmol. Yield: 14%) $^1$H NMR (400 MHz, CDCl$_3$): δ (ppm) 9.08-9.07 (d, J=1.5 Hz, 2H), 8.81 (d, J=2.0 Hz, 2H), 8.59 (d, J=1.8 Hz, 2H), 8.45 (d, J=1.1 Hz, 2H), 8.41 (d, J=1.7 Hz, 2H), 8.05-8.04 (d, J=2.0 Hz, 2H), 7.78-7.76 (dd, J=8.4 Hz, 1.1 Hz, 2H), 7.43-7.41 (dd, J=8.5 Hz, 1.7 Hz, 2H), 7.38-7.36 (d, J=8.3 Hz, 2H), 7.31-7.29 (d, J=8.5 Hz, 2H), 7.03-7.01 (d, J=8.9 Hz, 4H), 6.98 (s, 2H), 6.78-6.76 (d, J=8.9 Hz, 4H), 5.01 (s, 1H), 4.30-4.25 (m, 4H), 3.73 (s, 6H), 1.38-1.36 (m, 6H). $^{13}$C NMR (100 MHz, CDCl$_3$): δ (ppm) 158.9, 156.1, 154.8, 151.2, 148.2, 147.8, 147.0, 140.7, 139.9, 136.9, 136.8, 136.6, 132.0, 131.7, 129.0, 128.2, 125.5, 125.4, 124.9, 123.5, 123.5, 121.3, 120.0, 118.7, 114.2, 109.2, 108.4, 60.7, 55.2, 37.9, 31.9, 30.3, 22.7, 13.8. HRMS: m/z calcd for [M+H$^+$] C$_{64}$H$_{45}$O$_2$N$_6$Br$_2$: 1087.1965; found: 1087.1964. Its 1H-NMR (the full spectrum and the area where the aromatic zone is enlarged) is shown in FIG. 9 for details.

Figure 10:
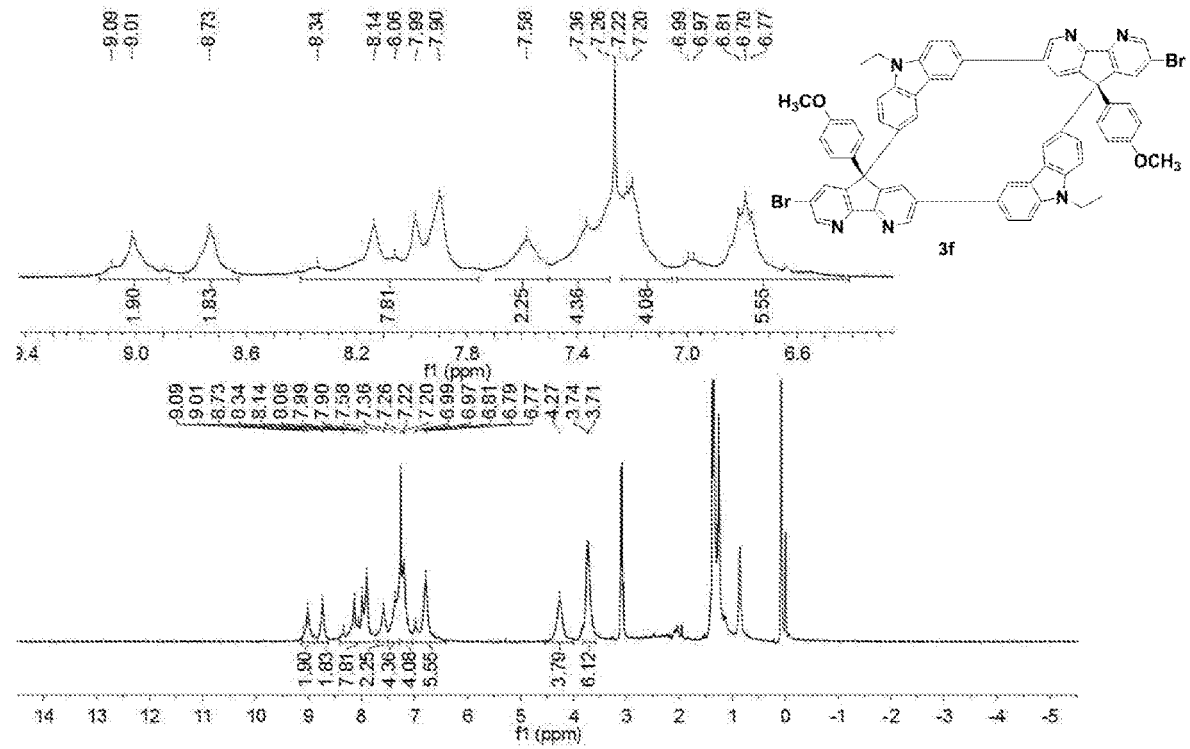
FIG. 10 shows the 1H-NMR of organic nanogrid 3f.

3f (89 mg, 0.082 mmol. Yield: 61%) $^1$H NMR (400 MHz, CDCl$_3$): δ (ppm) 9.09-9.01 (2H), 8.73 (2H), 8.34-7.90 (8H), 7.58 (2H), 7.36-7.10 (8H), 6.99-6.77 (6H). 4.27 (4H), 3.74-3.71 (6H), 1.29-1.24 (6H). $^{13}$C NMR (100 MHz, CDCl$_3$): δ (ppm) 159.1, 155.9, 154.3, 151.1, 149.3, 148.6, 147.2, 140.3, 139.7, 139.3, 138.1, 137.5, 136.4, 135.4, 134.0, 132.6, 131.9, 129.1, 128.8, 127.7, 126.3, 125.7, 124.4, 123.5, 123.2, 122.9, 120.5, 119.7, 119.5, 114.3, 114.1, 109.3, 61.1, 55.3, 46.1, 32.0, 13.9, 8.6. Its 1H-NMR (the full spectrum and the area where the aromatic zone is enlarged) is shown in FIG. 10 for details.

Embodiment Case 4: Preparation of Organic Nanogrids 4d and 4e

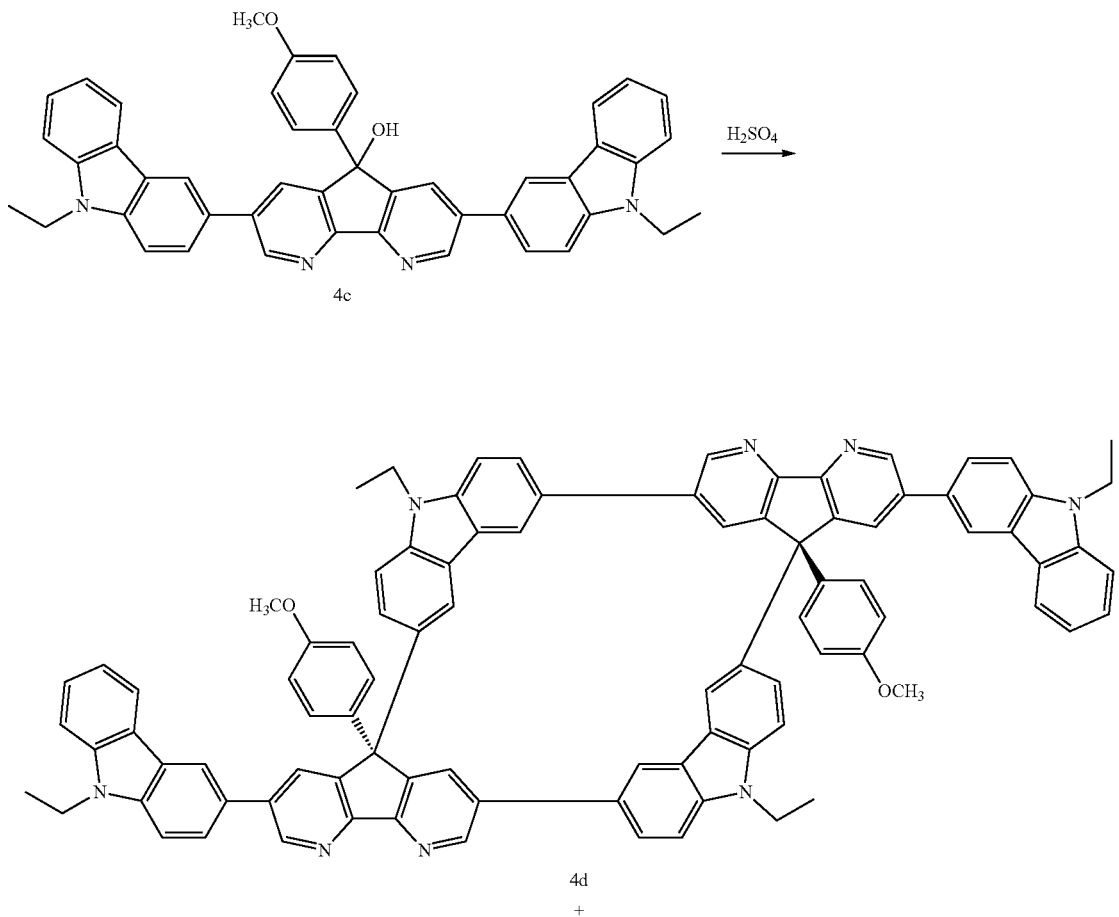

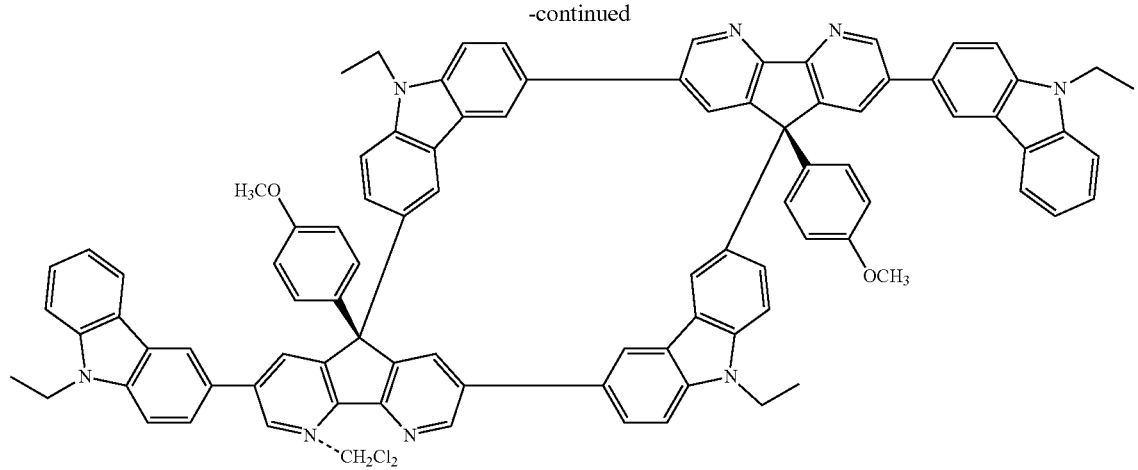

4e

Add 4c (100 mg, 0.15 mol, 1 equiv) into a small reaction flask, and then add 0.5 mL of dichloromethane into the flask. After stirring the resulted solution for 30 min, add concentrated sulfuric acid (0.12 mL, 2.25 mmol, 15 equiv) into it quickly. Use the thin layer chromatography to monitor if the reaction of the raw materials has been basically complete. If yes, add potassium hydroxide aqueous solution to quench the reaction. Extract the resulted solution with dichloromethane, collect the organic phase, remove the solvent with rotary evaporation, and further separate and purify the organic phase with column chromatography to obtain light yellow solid powder 4d and 4e.

Figure 11:
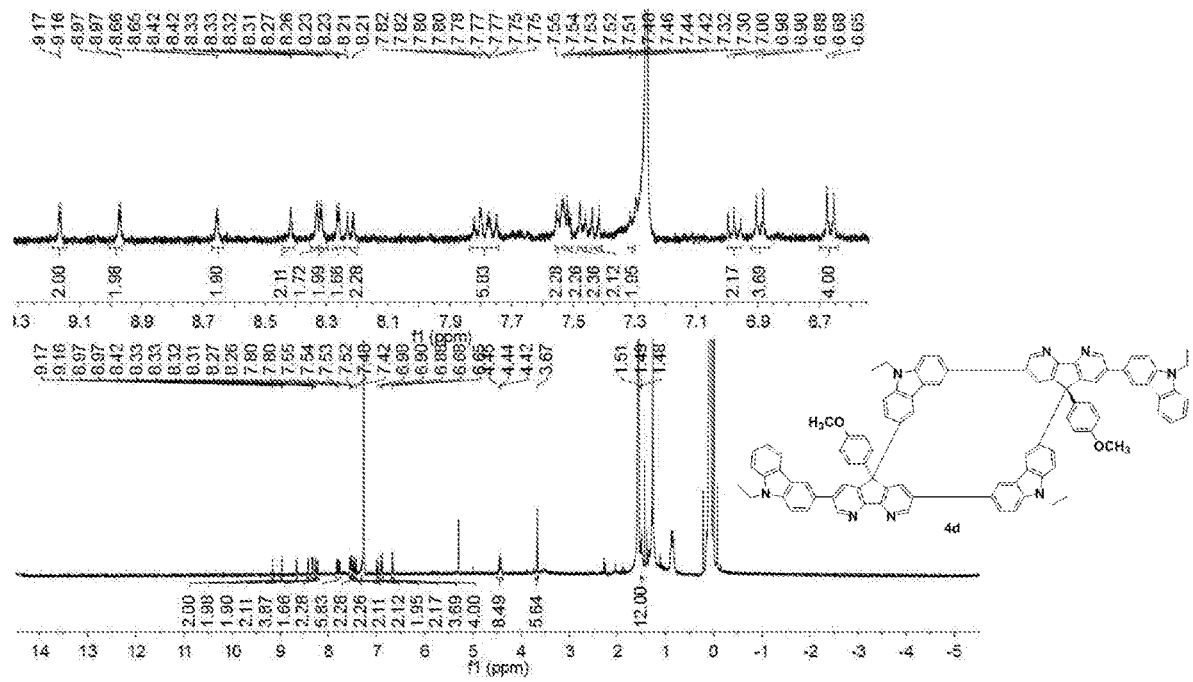
FIG. 11 shows the 1H-NMR of organic nanogrid 4d.

4d (30 mg, 0.023 mmol. Yield: 30%) $^1$H NMR (400 MHz, CDCl$_3$): δ (ppm) 9.17-9.16 (d, J=1.9 Hz, 2H), 8.97 (d, J=1.7 Hz, 2H), 8.66-8.65 (d, J=1.3 Hz, 2H), 8.42 (d, J=1.2 Hz, 2H), 8.33 (d, J=1.4 Hz, 2H), 8.32-8.31 (d, J=1.9 Hz, 2H), 8.27-8.26 (d, J=2.1 Hz, 2H), 8.23-8.21 (dd, J=7.5, 0.6 Hz, 2H), 7.82-7.75 (m, 6H), 7.55-7.51 (m, 4H), 7.48-7.46 (d, J=8.4 Hz, 2H), 7.44-7.42 (d, J=9.4 Hz, 2H), 7.32-7.20 (m, 2H), 7.00-6.96 (t, J=8.0 Hz, 2H), 6.90-6.88 (d, J=8.8 Hz, 4H), 6.68-6.65 (d, J=9.0 Hz, 4H), 4.45-4.42 (m, 8H), 3.67 (s, 6H), 1.51-1.48 (m, 12H). MALDI-TOF-MS: m/z calcd for [M+H$^+$] C$_{92}$H$_{68}$O$_2$N$_8$: 1317.549; found: 1317.909. Its 1H-NMR (the full spectrum and the area where the aromatic zone is enlarged) is shown in FIG. 11 for details.

Figure 12:
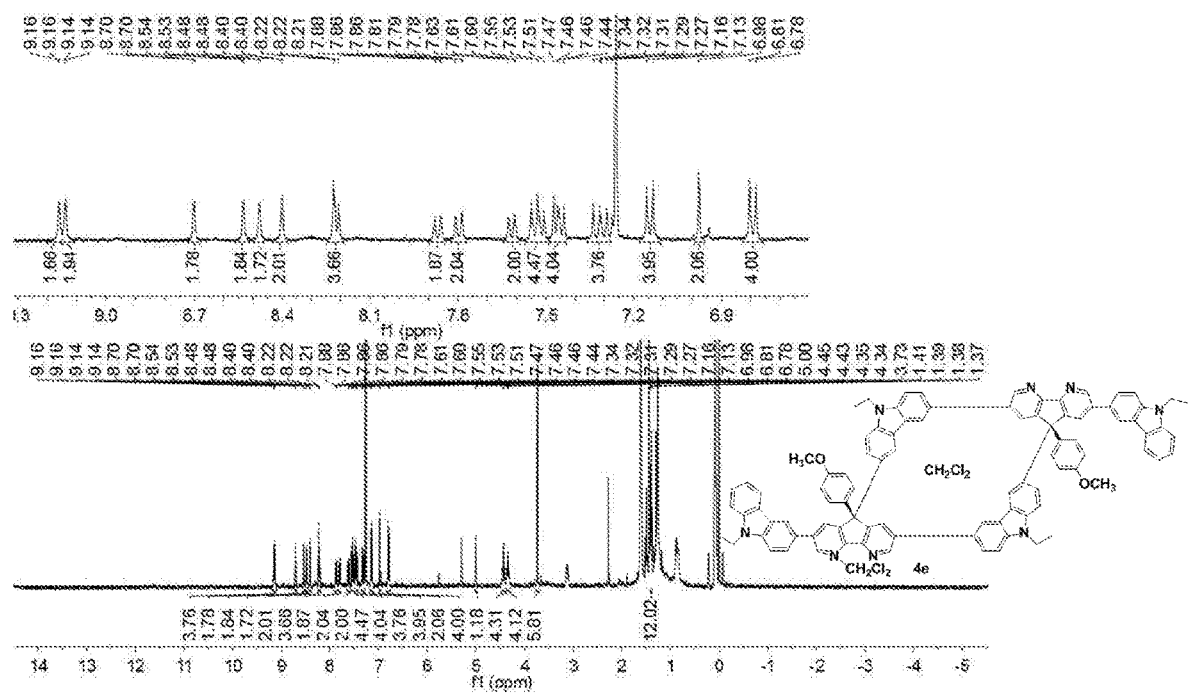
FIG. 12 shows the 1H-NMR of organic nanogrid 4e.

4e (10 mg, 0.008 mmol. Yield: 10%) $^1$H NMR (400 MHz, CDCl$_3$): δ (ppm) 9.16 (d, J=1.4 Hz, 2H), 9.14 (d, J=1.8 Hz, 2H), 8.70 (d, J=1.8 Hz, 2H), 8.54-8.53 (d, J=1.6 Hz, 2H), 8.48 (d, J=1.7 Hz, 2H), 8.40 (d, J=1.8 Hz, 2H), 8.22-8.21 (m, 4H), 7.88-7.86 (dd, J=8.1, 1.3 Hz, 2H), 7.81-7.78 (dd, J=8.2, 1.5 Hz, 2H), 7.63-7.60 (dd, J=8.6, 2.2 Hz, 2H), 7.55-7.51 (m, 4H), 7.47-7.44 (m, 4H), 7.34-7.27 (m, 4H), 7.16-7.13 (d, J=8.8 Hz, 4H), 6.98 (s, 2H), 6.81-6.78 (d, J=8.9 Hz, 4H), 5.00 (s, 1H), 4.47-4.41 (q, J=6.5 Hz, 4H), 4.37-4.33 (m, 4H), 3.73 (s, 6H), 1.41-1.37 (m, 12H). $^{13}$C NMR (100 MHz, CDCl$_3$): δ (ppm), 159.0, 158.6, 155.8, 155.7, 155.7, 149.1, 149.0, 147.1, 146.6, 140.4, 139.9, 139.7, 138.1, 138.1, 137.7, 132.8, 132.1, 132.1, 132.0, 129.2, 129.1, 129.1, 128.9, 128.3, 127.5, 127.4, 126.6, 126.2, 125.3, 125.3, 124.5, 124.0, 123.7, 123.3, 122.9, 122.9, 120.6, 120.6, 119.5, 119.5, 119.3, 119.1, 114.2, 114.2, 113.9, 113.9, 60.5, 58.1, 55.3, 55.2, 37.9, 37.7, 34.9, 34.6, 31.5, 30.3, 30.2, 29.7, 29.4, 28.7, 28.2, 22.7, 14.2, 13.9, 13.9, 8.1. MALDI-TOF-MS: m/z calcd for [M+H$^+$] C$_{92}$H$_{68}$O$_2$N$_8$: 1317.549; found: 1316.957. Its 1H-NMR (the full spectrum and the area where the aromatic zone is enlarged) is shown in FIG. 12 for details.

Embodiment Case 5: Preparation of Nanopolymer Through the Nano-Connection Mode

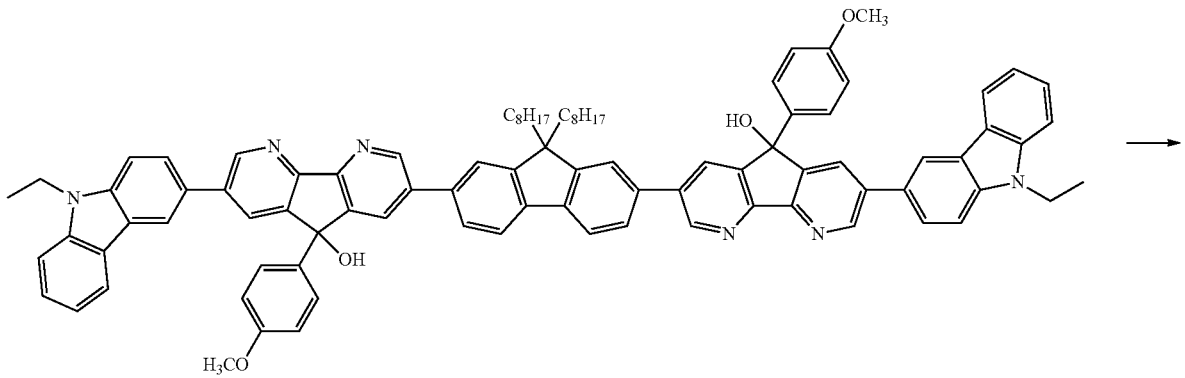

5c

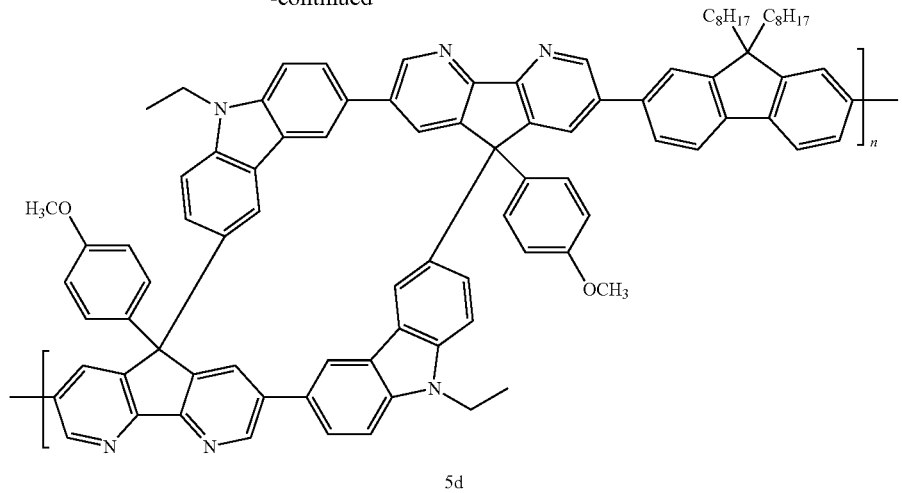

5d

Figure 13:
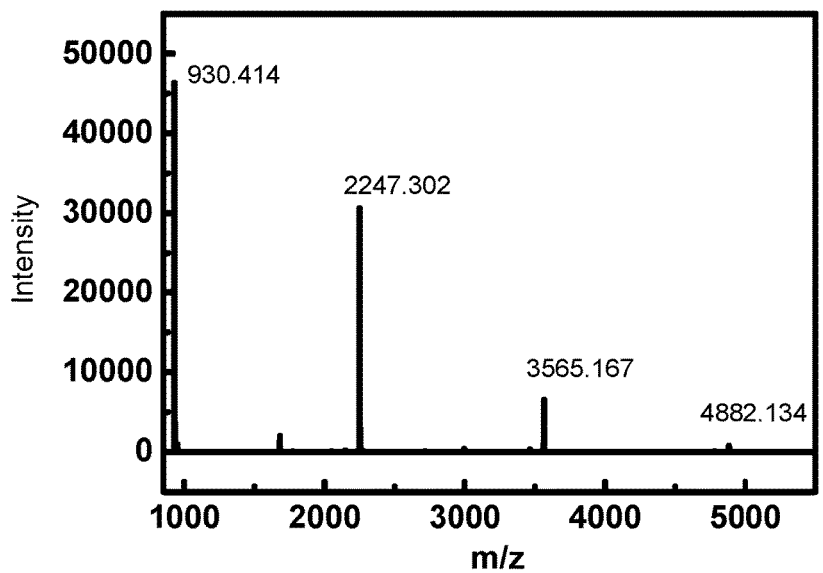
FIG. 13 shows the time-of-flight mass spectrogram of the reaction solution in the polymerization formula (V) (Friedel-Crafts polymerization) of the nanopolymer.
Figure 14:
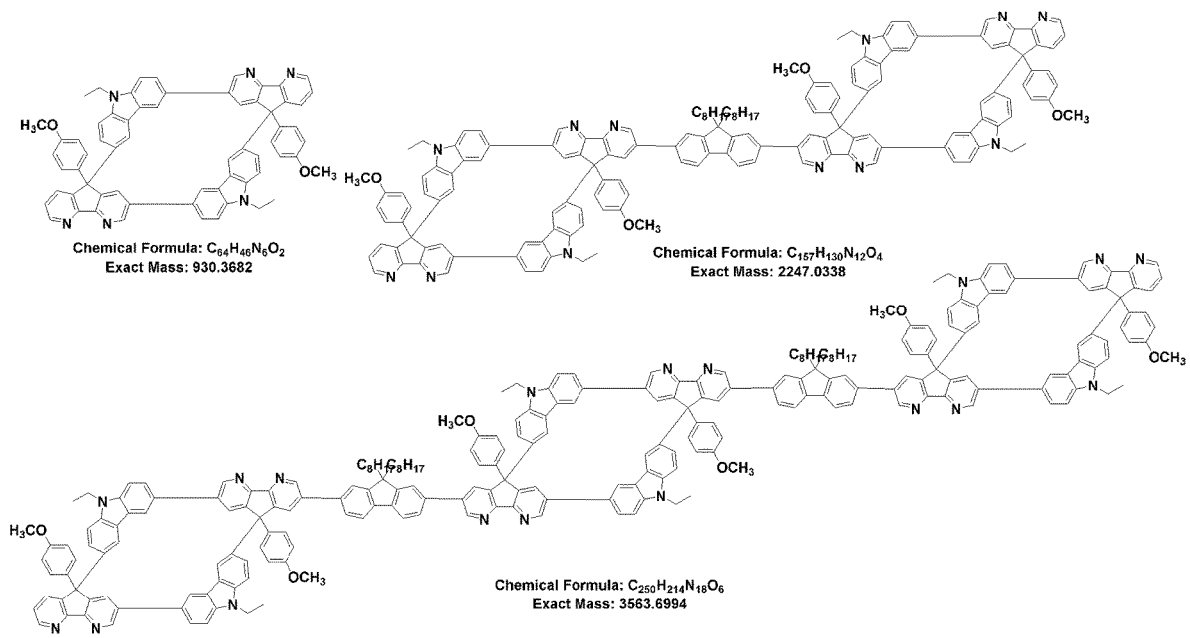
FIG. 14 shows various oligomeric grids derived from polymerization formula (V) as well as their molecular weights.
Figure 15:
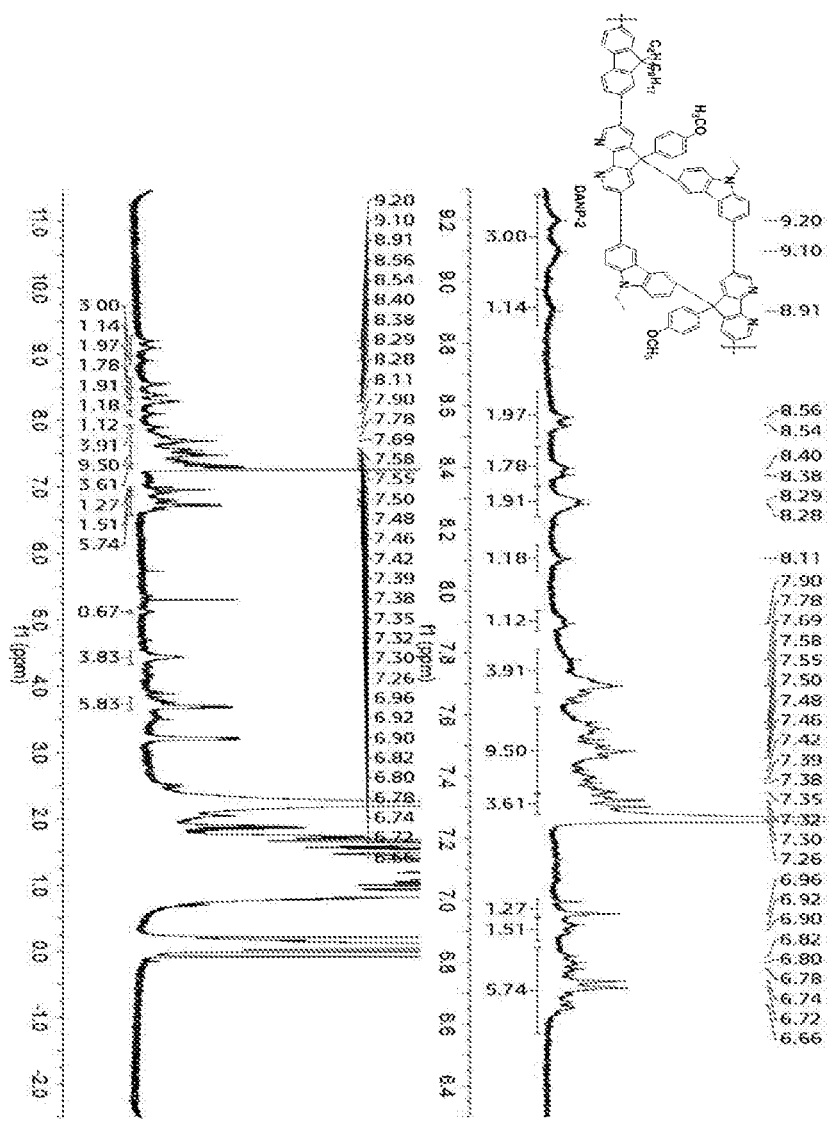
FIG. 15 shows the 1H-NMR of nanopolymer 5d.
Figure 16:
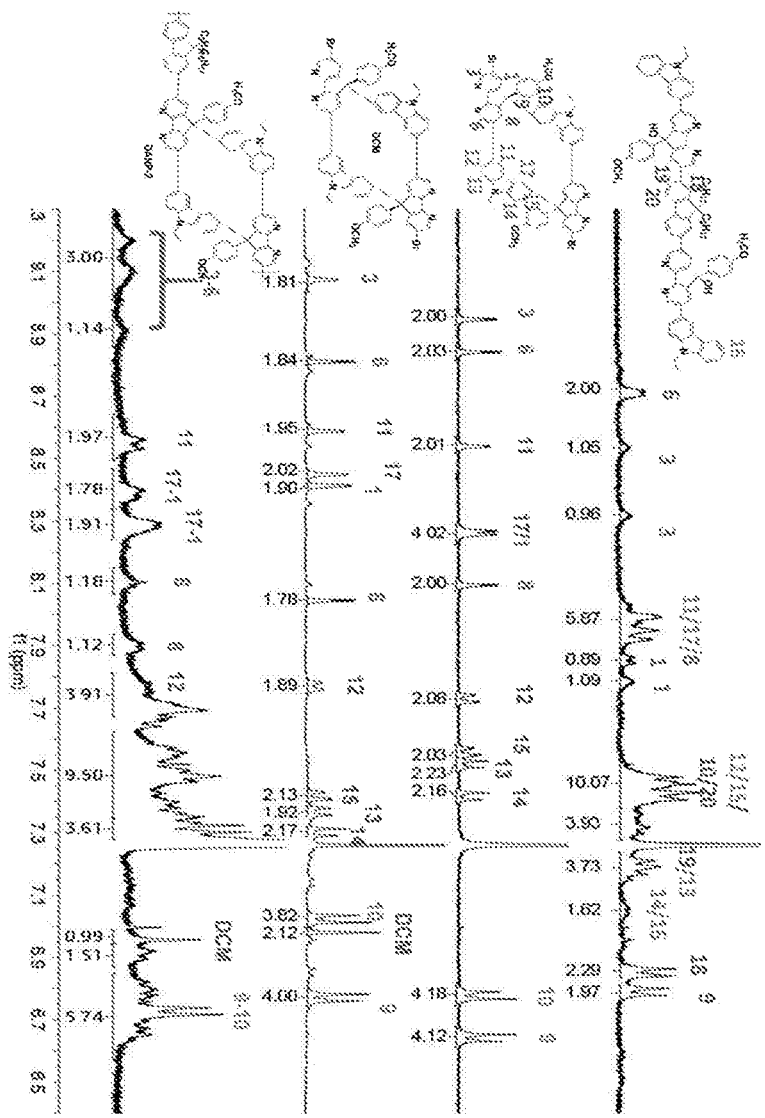
FIG. 16 compares the 1H-NMR of nanopolymer 5d with those of other similar compounds.
Figure 17:
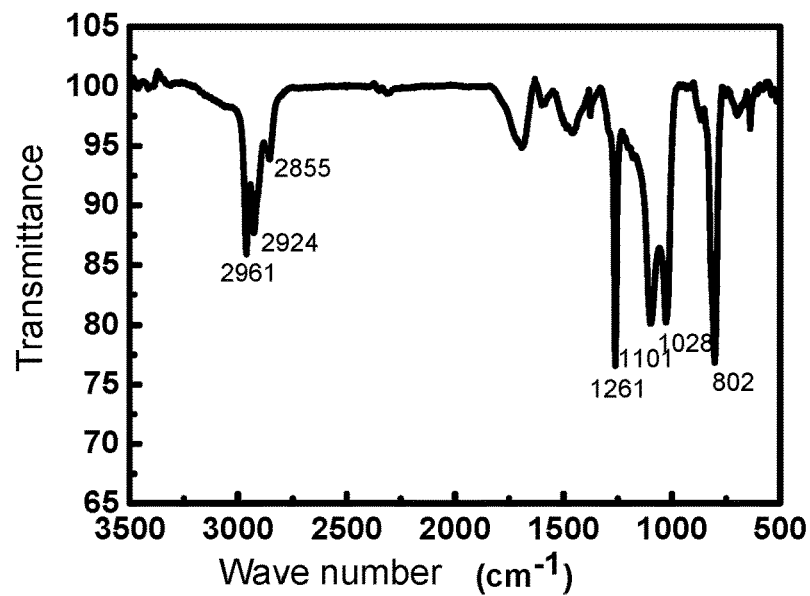
FIG. 17 shows a single infrared spectrum of nanopolymer 5d.
Figure 18:
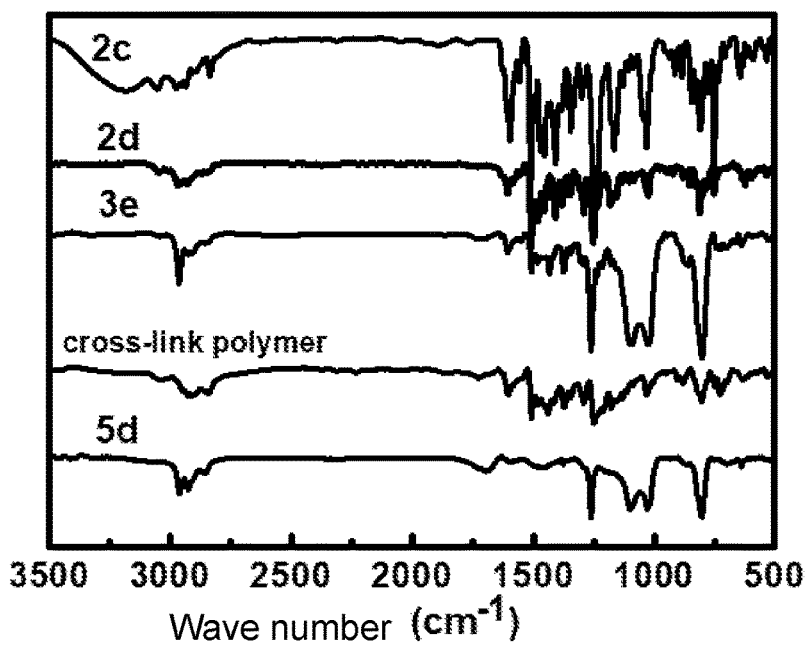
FIG. 18 compares the infrared spectrum of nanopolymer 5d with those of other similar compounds.
Figure 19:
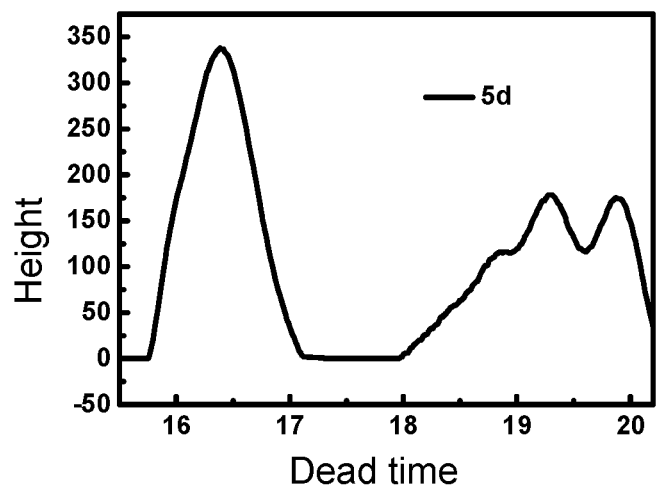
FIG. 19 shows the GPC test chart of nanopolymer 5d.
Figure 20:
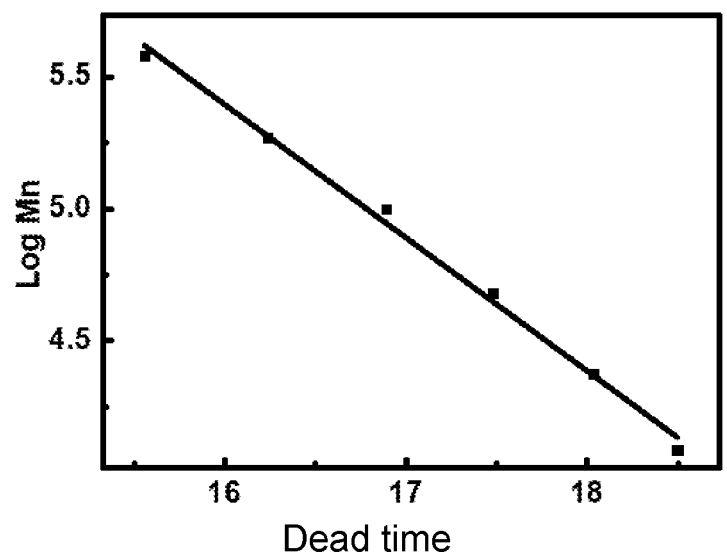
FIG. 20 shows the linear fitting curve in the GPC test of nanopolymer 5d.

Add 5c (78 mg, 0.06 mol, 1 equiv) into a small reaction flask, then add 4 mL of dichloromethane into the flask, and then add trifluoromethanesulfonic acid (0.10 mL, 1.20 mmol, 60 equiv) into the flask quickly, and then add the end-capping group into the flask after 1 min. After the reaction goes on for 1 h, add potassium hydroxide aqueous solution into the flask to quench the reaction. Extract the resulted solution with dichloromethane, collect the organic phase and remove the solvent with rotary evaporation to obtain yellow solid powder 5d. From the time-of-flight mass spectrogram (FIG. 13) of the reaction solution in the Friedel-Crafts polymerization reaction (polymerization formula (V)), it can be found that the molecular weight of the product in the reaction solution is 930.414, 2247.302, 3565.167 and 4882.134, which can correspond to mono-grid, two-grid, three-grid and four-grid oligomers, respectively. The molecular structure and molecular weight of the mono-grid, two-grid and three-grid compounds are shown in FIG. 14. The structures of the polymers are characterized with NMR, GPC and infrared spectroscopy. The NMR of the mono-grid compound is shown in FIG. 15. The signal peak of this compound is relatively clear, and it does not show any large bulge, indicating that this nanopolymer is a rigid polymer, and it is difficult to bend the chain. In order to accurately confirm its configuration, we compared its nuclear magnetic stack spectra with those of similar monomers (as shown in FIG. 16), and found that most of the nanopolymer's signal peaks can correspond to 3d and 3e, and the ratio is approximately 1:1. On the single infrared spectrum of the nanopolymer (as shown in FIG. 17), it is found that its characteristic peaks with relatively strong infrared absorption are: 2961, 2924, 2855, 1261, 1101, 1028, and 802. We further compared them with those of other similar compounds (the infrared spectrum comparison chart is shown in FIG. 18) and found that the characteristic peak of 5d matches that of compound 3e very highly, but its infrared spectrum is very different from those of cross-link polymers with poor solubility, which are not nanopolymers. This proves the regular structure of the nanopolymer. FIG. 19 is the GPC test chart of this nanopolymer. It can be found that, in addition to oligomers with small molecular weight, there are also polymers with high molecular weight (approximately 80,000 Da) in the nanopolymer. The linear fitting curve of this GPC test is shown in FIG. 20, which uses 5 points to make a linear fitting relationship between the logarithm of mass (Log Mn) and the dead time. The relationship formula is: $y=-0.2062*X+8.04259$.

What is claimed is:

1. A nanopolymer, wherein its general formula is (II):

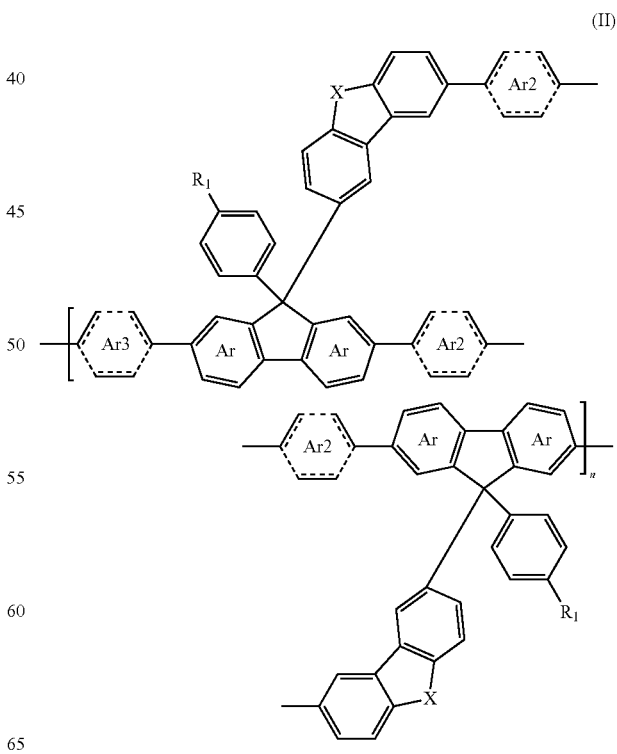

(II)

wherein, R₁ includes hydrogen or alkoxy chain;
X is N atom, where the following structures can be introduced on N atoms:

—H—C$_n$H$_{2n+1}$;

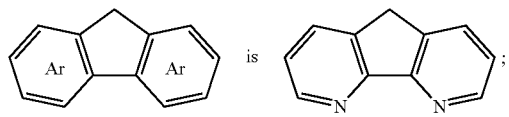 is is

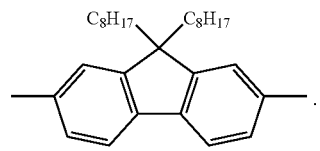

2. A method for preparing the nanopolymer mentioned in claim 1, wherein the corresponding organic nanopolymer is obtained from brominated organic nanogrids through the C—C bond coupling reaction,

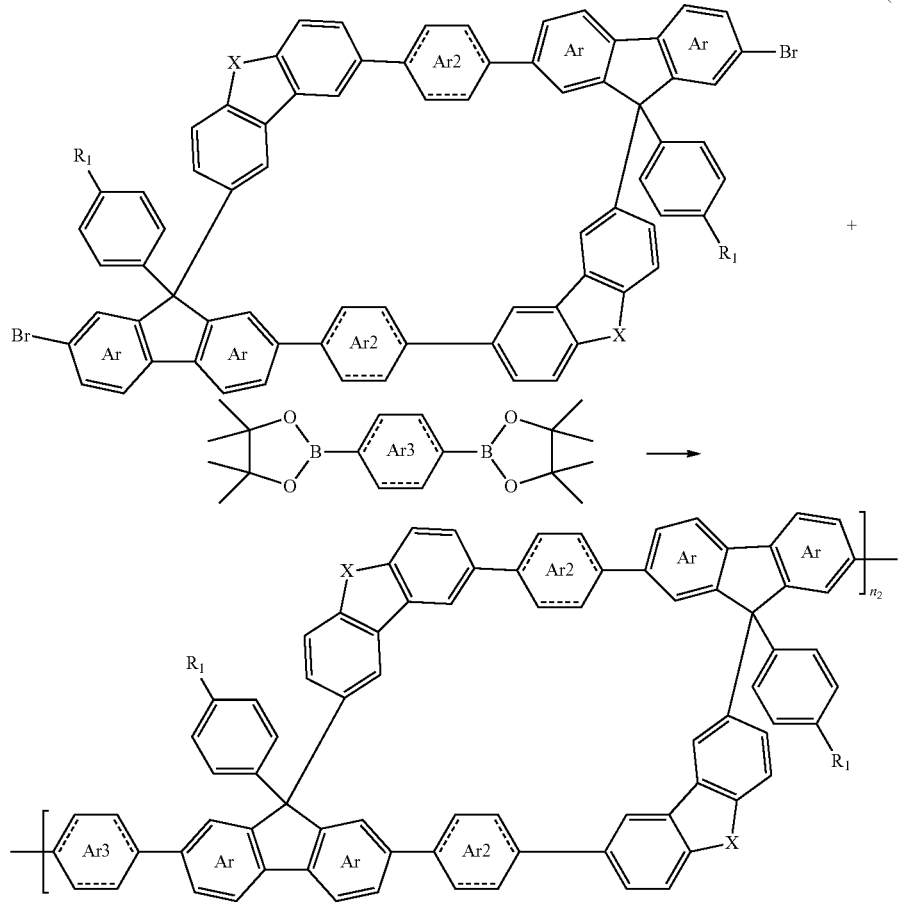

(IV)

-continued

is non-existent;
wherein, n is a natural number from 1 to 10;

wherein, the reaction route is reaction formula (IV).

3. A method for preparing the nanopolymer mentioned in claim 1, wherein the organic nanopolymer is obtained from A₂B₂ polymerization monomers directly through the Friedel-Crafts polymerization,

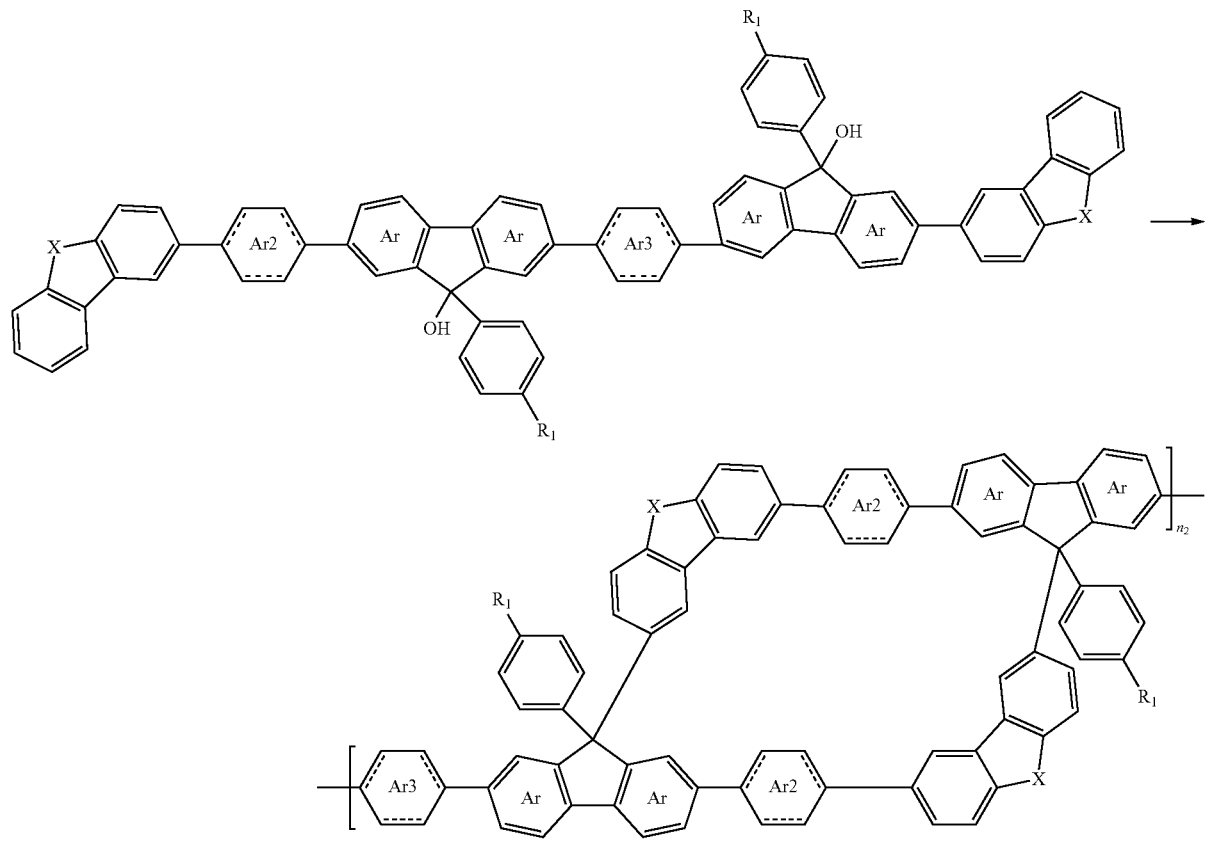
wherein, the reaction route is reaction formula (V).
* * * * *